United States Patent
During

(10) Patent No.: US 10,765,646 B2
(45) Date of Patent: Sep. 8, 2020

(54) METHODS OF TREATING DEVELOPMENTAL ENCEPHALOPATHIES

(71) Applicant: Ovid Therapeutics Inc., New York, NY (US)

(72) Inventor: Matthew During, Weston, CT (US)

(73) Assignee: OVID THERAPEUTICS INC., New York, NY (US)

(*) Notice: Subject to any disclaimer, the term of this patent is extended or adjusted under 35 U.S.C. 154(b) by 0 days.

(21) Appl. No.: 15/951,580

(22) Filed: Apr. 12, 2018

(65) Prior Publication Data
US 2018/0296501 A1    Oct. 18, 2018

Related U.S. Application Data

(60) Provisional application No. 62/485,211, filed on Apr. 13, 2017, provisional application No. 62/501,885, filed on May 5, 2017.

(51) Int. Cl.
| | | |
|---|---|---|
| *A61K 31/135* | (2006.01) | |
| *A61K 9/00* | (2006.01) | |
| *A61P 25/08* | (2006.01) | |
| *A61P 25/28* | (2006.01) | |
| *A61K 9/20* | (2006.01) | |

(52) U.S. Cl.
CPC .......... *A61K 31/135* (2013.01); *A61K 9/0043* (2013.01); *A61K 9/2009* (2013.01); *A61K 9/2013* (2013.01); *A61K 9/2018* (2013.01); *A61K 9/2054* (2013.01); *A61K 9/2077* (2013.01); *A61K 9/2081* (2013.01); *A61P 25/08* (2018.01); *A61P 25/28* (2018.01)

(58) Field of Classification Search
CPC ..... A61K 31/135; A61K 9/0043; A61P 25/08; A61P 25/10; A61P 25/12
See application file for complete search history.

(56) References Cited

U.S. PATENT DOCUMENTS

| | | | |
|---|---|---|---|
| 2012/0021943 A1 | 1/2012 | Tavares et al. | |
| 2014/0222473 A1* | 8/2014 | Patel et al. | C07C 215/44 514/462 |
| 2014/0275277 A1* | 9/2014 | Basstanie | A61K 9/0043 514/646 |
| 2014/0343044 A1 | 11/2014 | Ceulemens et al. | |
| 2016/0199304 A1* | 7/2016 | Nivorozhkin et al. | A61K 9/2059 514/1 |
| 2017/0036707 A1 | 2/2017 | Shinohara et al. | |

FOREIGN PATENT DOCUMENTS

WO    2016073653 A1    5/2016

OTHER PUBLICATIONS

Mewasingh et al., "Oral ketamine in paediatric non-convulsive status epilepticus," Seizure 2003; 12: 483-489. (Year: 2003).*
Höfler et al. "(S)-Ketamine in Refractory and Super-Refractory Status Epilepticus: A Retrospective Study," CNS Drugs Sep. 2016;30(9):869-76. PMID: 27465262. (Year: 2016).*
Corrigan et al., "Safety and efficacy of intranasally administered medications in the emergency department and prehospital settings," Am. J. Health Syst. Pharm. Sep. 15, 2015;72(18):1544-54. PMID: 26346210. (Year: 2015).*
Kim et al., "The Effects of Long-Term Ketamine Treatment on Cognitive Function in Complex Regional Pain Syndrome: A Preliminary Study", Pain Medicine 2016; vol. 17, Psychology, Psychiatry, Imaging and Brain Neuroscience Section; pp. 1447-1451.
International Preliminary Report on Patentability dated Mar. 3, 2020, corresponding to counterpart International Application No. PCT/US2018/027276 and Written Opinion of the International Searching Authority, corresponding to counterpart International Application No. PCT/US2018/027276; 6 total pages.
Fang et al., "Ketamine for the Treatment of Refractory Status Epilepticus," Seizure, vol. 30, pp. 14-20 (2015).
Mohammad et al., "Symptomatic Treatment of Children with Anti-NMDAR Encephalitis," Developmental Medicine & Child Neurology, (2016), vol. 58; pp. 376-384.

* cited by examiner

*Primary Examiner* — Theodore R. West
(74) *Attorney, Agent, or Firm* — Carter, DeLuca & Farrell LLP

(57) ABSTRACT

Methods of treating developmental encephalopathies by administering compositions including ketamine, norketamine, or other derivatives of ketamine, or a pharmaceutically acceptable salt of any of the foregoing, are provided. The methods and compositions may be used to treat conditions such as Dravet syndrome.

12 Claims, No Drawings

METHODS OF TREATING DEVELOPMENTAL ENCEPHALOPATHIES

CROSS REFERENCE TO RELATED APPLICATIONS

This application claims benefit of and priority to U.S. Provisional Application No. 62/485,211, filed Apr. 13, 2017 and U.S. Provisional Application No. 62/501,885, filed May 5, 2017, which are incorporated herein by reference in their entirety.

TECHNICAL FIELD

Methods of using a composition including ketamine, norketamine, derivatives thereof, and/or pharmaceutically acceptable salts thereof for the treatment of developmental encephalopathies.

BACKGROUND

Ketamine, also known as (R,S)-2-(2-chlorophenyl)-2-(methylamino)cyclohexanone, is a noncompetitive N-methyl-D-aspartate receptor antagonist that has been in use as a dissociative anesthetic for over fifty years. More recently, ketamine has been used in treating other conditions, for example, to alleviate pain, depression, symptoms associated with acute brain injury and stroke, epilepsy, alcohol dependence, Alzheimer's disease, asthma and other disorders. Non-competitive NMDA receptor antagonism may be associated with the analgesic effects; opiate receptor binding may contribute to analgesia and dysphoric reactions; and sympathomimetic properties may result from enhanced central and peripheral monoaminergic transmission. Ketamine appears to block dopamine uptake and therefore elevates synaptic dopamine levels. Ketamine is available as a racemic mixture. It has been commercially supplied as the hydrochloride salt in 0.5 mg/mL and 5 mg/mL ketamine base equivalents. For induction of 5-10 minutes of surgical anesthesia, a dose of 1.0-4.5 mg/kg may be intravenously administered; 6.5-13 mg/kg may be given intramuscularly for 12-25 minutes of surgical anesthesia.

Norketamine, or N-desmethylketamine, also known as (R,S)-2-(2-chlorophenyl)-2-(amino)cyclohexanone, is the major active metabolite of ketamine which is subject to the first-pass liver metabolism via N-demethylation. Like ketamine, norketamine acts as a noncompetitive NMDA receptor antagonist ($K_i$=1.7 µM and 13 µM for (S)-(+)-norketamine and (R)-(−)-norketamine, respectively), but is about 3-5 times less potent as an anesthetic in comparison. The elimination half-life of ketamine has been estimated at 2-3 hours, and 4 hours for norketamine.

Recently, it has been shown that frequent or chronic use of ketamine may cause impaired cognitive function. For example, people who chronically abuse ketamine have been shown to demonstrate impaired cognitive processing speed, verbal learning, and episodic, semantic, and working memory compared with healthy controls. See, e.g., Kim et al., Pain Medicine 2016; 17:1447-1451.

Dravet syndrome is a form of developmental encephalopathy associated with mutations of the SCN1A and SCN2A genes. According to the Dravet Syndrome Foundation, it is a rare, catastrophic, disease that begins in the first year of life with frequent and/or prolonged seizures. Dravet syndrome affects 1:15,700 individuals, 80% of whom have a mutation in their SCN1A gene. While seizures persist, other comorbidities such as developmental delay and abnormal EEGs are often not evident until the second or third year of life. Other than seizures, common issues associated with Dravet syndrome include behavioral and developmental delays, movement and balance issues, orthopedic conditions, delayed language and speech issues, growth and nutrition issues, sleeping difficulties, chronic infections, sensory integration disorders, and disruptions of the autonomic nervous system (e.g., regulation of body temperature and sweating). Current treatment options are limited, and the constant care required for someone suffering from Dravet syndrome can severely impact the patient's and the family's quality of life. Patients with Dravet syndrome face a 15-20% mortality rate.

SUMMARY

Methods of treating a developmental encephalopathy are provided that include administering to a patient in need thereof ketamine, norketamine or a pharmaceutically acceptable salt of either ketamine or norketamine. In embodiments, a method of treating a developmental encephalopathy includes administering to a patient in need thereof an effective amount of ketamine or a derivative thereof. In embodiments, a method of treating a developmental encephalopathy includes administering to a patient in need thereof an effective amount of norketamine or a derivative thereof. In embodiments, the developmental encephalopathy can be Dravet syndrome, infantile spasms, catastrophic epilepsy, Lennox-Gastaut syndrome, West syndrome, tuberous sclerosis, Ohtahara syndrome, early myoclonic encephalopathy, early-onset epileptic encephalopathy, epilepsy with myoclonic-atonic seizures, status epilepticus, and/or non-convulsive status epilepticus. In embodiments, the developmental encephalopathy is associated with a genetic mutation of a one or more of the following genes: ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, GABRA1, GABRB3, GABRG2, GNAO1, GOSR2, GRIN1, GRIN2A, GRIN2B, HCN1, HNRNPU, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, PURA, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX. In embodiments, the developmental encephalopathy is associated with a genetic mutation of a one or more of the following genes: ALG13, CDKL5, GABRB3, DNM1, HCN1, GRIN2A, GABRA1, GNAO1, KCNT1, SCN2A, SCN8A, and SLC35A2. In embodiments, the developmental encephalopathy is associated with a genetic mutation of a one or more of the following genes: SCN1A, PCDH19, CHD2, SCN8A, GABRA1, and STXBP1. In embodiments, the developmental encephalopathy is ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, GABRA1, GABRB3, GABRG2, GNAO1, GOSR2, GRIN1, GRIN2A, GRIN2B, HCN1, HNRNPU, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX encephalopathy. In embodiments, the developmental encephalopathy is CDKL5 encephalopathy. In embodiments, the developmental encephalopathy is associated with one or more of the following genes: ALG13, DNM1, FOXG1 duplications, GABRA1, GABRB3, GRIN1, GRIN2A, GRIN2B, IQSEC2, KCNT1, MAGI2, MEF2C, NEDDL4, NDP, NRXN1, PIGA, PLCB1, PTEN, SCA2, SCN1A, SCN2A, SCN8A, SETBP1, SIK1, SLC25A22, SLC35A2, SPTAN1, ST3GAL3, STXBP1, TBC1D24, and TCF4. In embodiments, the developmental encephalopathy is associated with one or more of the following genes: SCN1A, GABRA1, GABRG2, HCN1, KCNA2, SCN1B, and STXBP1. In embodiments, the developmental encephalopathy is associated with one or more of the following genes: ALG13, DNM1, FLNA, GABRB3, GLI3, HNRNPU, SCN1A, SCN2A, SCN8A, and STXBP1. In embodiments, the developmental encephalopathy is associated with one or more of the following genes: SLC2A1, SLC6A1, GABRA1, GABRG2, SCN1A, and SCN1B. In embodiments, the developmental encephalopathy is associated with one or more of the following genes: KCNT1, SCN2A, SCN1A, PLCB1, QARS, SCN8A, SLC25A22, TBC1D24, and SLC12A5. In embodiments, the developmental encephalopathy is associated with one or more of the following genes: KCNQ2, KCNT1, and PIGQ. In embodiments, the developmental encephalopathy is associated with one or more of the following genes: KCNT1, GRIN2A, GRIN2D and SCN8A. In embodiments, the ketamine or a derivative thereof may be one of more of ketamine, norketamine, neuro-attenuating ketamine (NAKET) and pharmaceutically acceptable salts thereof. In embodiments, the ketamine or a derivative thereof may be one or more of ketamine, norketamine, neuro-attenuating ketamine (NAKET), neuro-attenuating norketamine (NANKET) and pharmaceutically acceptable salts thereof. In embodiments, the patient is administered about 0.1 mg/kg to about 10.0 mg/kg of ketamine or a derivative thereof. In embodiments, the patient is administered about 0.1 mg/kg to about 5.0 mg/kg of ketamine or a derivative thereof. In embodiments, the patient is administered about 1 mg to about 50 mg of ketamine or a derivative thereof. In embodiments, the patient is administered a total daily dose of from about 10 mg to about 100 mg of ketamine or a derivative thereof. In embodiments, a method of treating Dravet syndrome is provided which includes administering to a patient in need thereof an effective amount of ketamine or a salt thereof.

DETAILED DESCRIPTION

In embodiments, provided herein are methods and compositions for treating developmental encephalopathy by administering to a patient in need thereof a pharmaceutical composition including ketamine, norketamine or a pharmaceutically acceptable salt of either ketamine or norketamine. In embodiments, a method of treating a developmental encephalopathy includes administering to a patient in need thereof an effective amount of ketamine or a derivative thereof or a pharmaceutical salt of ketamine or a pharmaceutical salt of a derivative of ketamine. In embodiments, a method of treating a developmental encephalopathy includes administering to a patient in need thereof an effective amount of norketamine or a derivative thereof or a pharmaceutical salt of norketamine or a pharmaceutical salt of a derivative of norketamine. In embodiments, the methods described herein may be used to treat developmental encephalopathies including Dravet syndrome, Landau-Kleffner Syndrome, Lennox-Gastaut syndrome (LGS), and West syndrome. In embodiments, the methods include treatment of Dravet syndrome.

In embodiments, the methods include treatment of developmental encephalopathy characterized by epileptic aphasias. Conditions in the epilepsy-aphasia spectrum typically begin in childhood, and include Landau-Kleffner syndrome (LKS), epileptic encephalopathy with continuous spike-and-wave during sleep syndrome (ECSWS), autosomal dominant rolandic epilepsy with speech dyspraxia (ADRESD), intermediate epilepsy-aphasia disorder (IEAD), atypical childhood epilepsy with centrotemporal spikes (ACECTS), and childhood epilepsy with centrotemporal spikes (CECTS).

In embodiments, the methods described herein may be used to treat developmental encephalopathy characterized as a mutation associated with one or more of the following genes: ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, GABRA1, GABRB3, GABRG2, GNAO1, GOSR2, GRIN1, GRIN2A, GRIN2B, HCN1, HNRNPU, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, PURA, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX. In embodiments, the methods described herein may be used to treat developmental encephalopathy characterized as a sodium channel protein type 1 subunit alpha (Scn1A)-related disorder such as Dravet syndrome, Lennox-Gastaut syndrome (LGS), infantile spasms, and vaccine-related encephalopathy.

In embodiments, the methods described herein may be used to treat Lennox-Gastaut syndrome. Lennox-Gastaut syndrome is a form of severe epilepsy that begins in childhood According to the National Institute of Health, US National Library of Medicine it is characterized by multiple types of seizures and intellectual disability. People with Lennox-Gastaut syndrome typically begin having frequent seizures in early childhood, usually between ages 3 and 8. More than three-quarters of affected individuals have tonic seizures, which cause the muscles to stiffen (contract) uncontrollably. These seizures occur most often during sleep. Also common are atypical absence seizures, which cause a partial or complete loss of consciousness. Additionally, many affected individuals have drop attacks, which are sudden episodes of weak muscle tone. Drop attacks can result in falls that cause serious or life-threatening injuries. Other types of seizures have been reported less frequently in people with Lennox-Gastaut syndrome.

Most of the seizures associated with Lennox-Gastaut syndrome are very brief. However, more than two-thirds of affected individuals experience at least one prolonged period of seizure activity known as nonconvulsive status epilepticus. These episodes can cause confusion and a loss of alertness lasting from hours to weeks. Almost all children with Lennox-Gastaut syndrome develop learning problems and intellectual disability associated with their frequent seizures. Because the seizures associated with this condition are difficult to control with medication, the intellectual disability tends to worsen with time. Some affected children develop additional neurological abnormalities and behavioral problems. Many also have delayed development of motor skills such as sitting and crawling. As a result of their seizures and progressive intellectual disability, most people with Lennox-Gastaut syndrome require help with some or all of the usual activities of daily living. However, a small percentage of affected adults live independently.

In embodiments, the methods described herein may be used to treat developmental encephalopathy characterized as a heterozygous germline mutation in the gene encoding the glutamate receptor, ionotropic, n-methyl-d-aspartate, subunit 2a, also known as the GRIN2a gene. Heterozygous germline mutations in the GRIN2A gene have been found in focal epilepsy with speech disorder (FESD), a childhood-onset seizure disorder with a highly variable phenotype. FESD represents an electroclinical spectrum that ranges from severe early-onset seizures associated with delayed psychomotor development, persistent speech difficulties, and mental retardation to a more benign entity characterized by childhood onset of mild or asymptomatic seizures associated with transient speech difficulties followed by remission of seizures in adolescence and normal psychomotor development. In embodiments, the methods described herein may be used to treat developmental encephalopathy characterized as a heterozygous germline mutation in the gene encoding the glutamate receptor, ionotropic, n-methyl-d-aspartate, subunit 2b, also known as the GRIN2b gene. Mutations in the GRIN2b gene have been associated with mental retardation, autosomal dominant 6 (MRD6). In addition, 2 different de novo heterozygous missense mutations in the GRIN2B gene have been associated with early infantile epileptic encephalopathy-27 (EIEE27). In embodiments, the methods described herein may be used to treat developmental encephalopathy characterized as a heterozygous germline mutation in the gene encoding the glutamate receptor, ionotropic, n-methyl-d-aspartate, subunit 2c, also known as the GRIN2c gene. Mutations in the GRIN2c gene may also be associated with mental retardation and epilepsy.

The methods described herein may be particularly useful for treating children and infants, and for treating developmental encephalopathies that onset during infancy or childhood. In embodiments, the subject of the disclosed method is a newborn, a baby, a toddler, a preschooler, a school-age child, a tween, or a teenager. In embodiments, the subject is 18 years old or younger, 12 years old or younger, 10 years old or younger, 8 years old or younger, 6 years old or younger, 4 years old or younger, 2 years old or younger, 1 year old or younger. In embodiments, the subject is an adult that is over eighteen years old.

In embodiments, the subject has an intellectual developmental disability (IDD) such as an Autism Spectrum Disorder (ASD). In embodiments, the subject of the disclosed method has developmental encephalopathy and an IDD or ASD disorder. Common IDD and ASD that are comorbid with developmental encephalopathies include, but are not limited to, fragile X syndrome (FXS), Rett syndrome (RTT), Angelman syndrome, Prader-Willi syndrome, Velocardiofacial syndrome, Smith-Lemli-Opitz syndrome, neuroligin mutations and "interneuronopathies" resulting from aristaless-related homeobox, X-linked (ARX) and Nueropilin 2 (NRP2) gene mutations.

In embodiments, methods and compositions are provided for treating developmental encephalopathy by administering to a patient in need thereof ketamine or a pharmaceutically acceptable salt thereof. Ketamine herein includes both racemic and enantiomerically enriched, e.g., enantiomerically pure forms. In embodiments, ketamine is racemic ketamine. In embodiments, ketamine is enantiomerically enriched in one enantiomer. In embodiments, ketamine is enriched in the S enantiomer. In embodiments, ketamine is enriched in the R enantiomer. In embodiments, methods and compositions are provided for treating developmental encephalopathy by administering to a patient in need thereof norketamine or a pharmaceutically acceptable salt thereof. Norketamine herein includes both racemic and enantiomerically enriched, e.g., enantiomerically pure forms. In embodiments, norketamine is racemic norketamine. In embodiments, norketamine is enantiomerically enriched in one enantiomer. In embodiments, norketamine is enriched in the S enantiomer. In embodiments, norketamine is enriched in the R enantiomer. In embodiments, methods and compositions are provided for treating developmental encephalopathy by administering to a patient in need thereof a ketamine derivative or a pharmaceutically acceptable salt thereof. Ketamine derivatives include norketamine, neuro-attenuating ketamine (NAKET), neuro-attenuating norketamine (NANKET) and pharmaceutically acceptable salts of any of the foregoing. Ketamine derivatives herein include deuterated species of ketamine and norketamine. Ketamine derivatives herein include both racemic and enantiomerically enriched, e.g., enantiomerically pure forms. In embodiments, a ketamine derivative is a racemic ketamine derivative. In embodiments, a ketamine derivative is enantiomerically enriched in one enantiomer. In embodiments, a ketamine derivative is enriched in the S enantiomer. In embodiments, a ketamine derivative is enriched in the R enantiomer. In embodiments, deuterated ketamine, deuterated norketamine or deuterated forms of other ketamine derivatives may be utilized.

The structure of ketamine may be depicted as

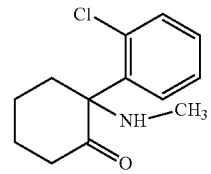 [SMILES: CNC1(c2ccccc2Cl)CCCCC1=O]

The structure of norketamine may be depicted as

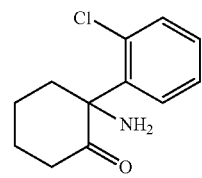 [SMILES: NC1(c2ccccc2Cl)CCCCC1=O]

Neuro-attenuating norketamine (NANKET) compounds may be represented by formula (I):

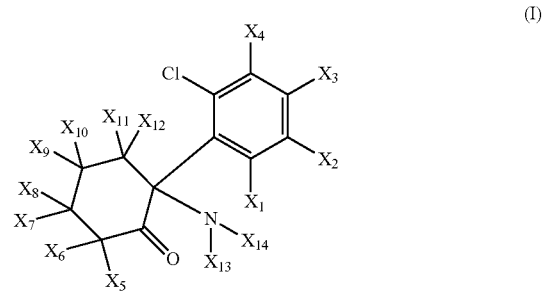

(I)

or a pharmaceutically acceptable salt thereof,
wherein $X_1$, $X_2$, $X_3$, $X_4$, $X_5$, $X_6$, $X_7$, $X_8$, $X_9$, $X_{10}$, $X_{11}$, $X_{12}$, $X_{13}$, and $X_{14}$ are each independently selected from the group consisting of hydrogen and deuterium, and wherein at least one of $X_1$, $X_2$, $X_3$, $X_4$, $X_5$, $X_6$, $X_7$, $X_8$, $X_9$, $X_{10}$, $X_{11}$, $X_{12}$, $X_{13}$, and $X_{14}$ is deuterium.

In embodiments of formula (I), when each of $X_1$, $X_2$, $X_3$, and $X_4$ is deuterium, then at least one of $X_5$, $X_6$, $X_7$, $X_8$, $X_9$, $X_{10}$, $X_{11}$, $X_{12}$, $X_{13}$, and $X_{14}$ is deuterium. In embodiments of formula (I), at least one of $X_5$, $X_6$, $X_7$, $X_8$, $X_9$, $X_{10}$, $X_{11}$, and $X_{12}$ is deuterium. In embodiments of formula (I), $X_5$, $X_6$, $X_7$, $X_8$, $X_9$, $X_{10}$, $X_{11}$, and $X_{12}$ are deuterium. In embodiments, $X_{13}$, and $X_{14}$ are deuterium. In embodiments of formula (I), $X_5$ and $X_6$ are deuterium, $X_7$ and $X_8$ are deuterium, $X_9$ and $X_{10}$ are deuterium, and/or $X_{11}$ and $X_{12}$ are deuterium. In embodiments of formula (I), $X_5$ and $X_6$ are deuterium. In embodiments of formula (I), $X_7$ and $X_8$ are hydrogen, $X_9$ and $X_{10}$ are hydrogen, and/or $X_{11}$ and $X_{12}$ are hydrogen. In embodiments, each of $X_7$, $X_8$, $X_9$, $X_{10}$, $X_{11}$, $X_{12}$, $X_{13}$, and $X_{14}$ is hydrogen. In embodiments of formula (I), $X_1$, $X_2$, $X_3$, and $X_4$, are deuterium. In embodiments of formula (I), $X_1$, $X_2$, $X_3$, and $X_4$, are hydrogen. In embodiments of formula (I), $X_5$, $X_6$, $X_7$, and $X_8$ are deuterium. In embodiments of formula (I), $X_5$, $X_6$, $X_7$, and $X_8$ are hydrogen. In embodiments of formula (I), $X_1$ and $X_{14}$ are deuterium. In embodiments of formula (I), $X_1$ and $X_{14}$ are hydrogen.

Neuro-attenuating ketamine (NAKET) compounds may be represented by formula (II):

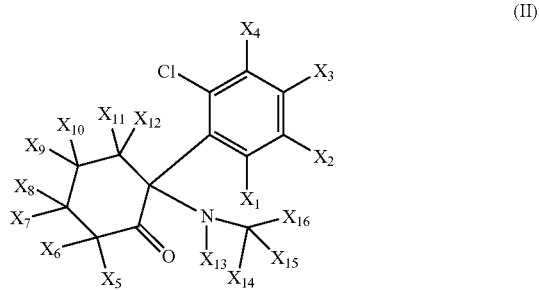

(II)

or a pharmaceutically acceptable salt thereof,
wherein $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$ and $X_{16}$ are each independently selected from the group consisting of hydrogen and deuterium, and wherein at least one of $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$ and $X_{16}$ is deuterium.

In embodiments of formula (II), $X_5$, $X_6$, $X_7$, $X_8$, $X_9$, $X_{10}$, $X_{11}$, and $X_{12}$ are deuterium. In embodiments of formula (II), $X_{14}$, $X_{15}$, and $X_{16}$ are deuterium. In embodiments of formula (II), $X_{14}$, $X_{15}$, and $X_{16}$ are hydrogen. In embodiments of formula (II), $X_{13}$ is hydrogen. In embodiments of formula (II), $X_{13}$ is deuterium. In embodiments of formula (II), $X_5$, $X_6$, $X_7$, $X_8$, $X_9$, $X_{10}$, $X_{11}$, and $X_{12}$ are deuterium; and $X_{14}$, $X_{15}$, and $X_{16}$ are deuterium. In embodiments of formula (II), $X_5$, $X_6$, $X_7$, $X_8$, $X_9$, $X_{10}$, $X_{11}$, and $X_{12}$ are deuterium; $X_{13}$ is deuterium; and $X_{14}$, $X_{15}$, and $X_{16}$ are deuterium. In embodiments of formula (II), $X_5$ and $X_6$ are deuterium, $X_7$ and $X_8$ are deuterium, $X_9$ and $X_{10}$ are deuterium, and/or $X_{11}$ and $X_{12}$ are deuterium. In embodiments of formula (II), $X_5$ and $X_6$ are deuterium. In embodiments of formula (II), $X_7$ and $X_8$ are hydrogen, $X_9$ and $X_{10}$ are hydrogen, and/or $X_{11}$ and $X_{12}$ are hydrogen. In embodiments, each of $X_7$, $X_8$, $X_9$, $X_{10}$, $X_{11}$, $X_{12}$, $X_{13}$, and $X_{14}$ is hydrogen. In embodiments of formula (II), $X_1$, $X_2$, $X_3$, $X_4$, are deuterium. In embodiments of formula (II), $X_1$, $X_2$, $X_3$, $X_4$, are hydrogen In embodiments of formula (II), $X_5$, $X_6$, $X_7$, $X_8$ are deuterium. In embodiments of formula (II), $X_5$, $X_6$, $X_7$, $X_8$ are hydrogen. In embodiments of formula (II), $X_{13}$ and $X_{14}$ are deuterium. In embodiments of formula (II), $X_{13}$ and $X_{14}$ are hydrogen.

Deuteration of pharmaceuticals to improve pharmacokinetics (PK), pharmacodynamics (PD), and toxicity profiles, has been demonstrated previously with some classes of drugs. See, e.g., PCT published application number WO2016/073653 incorporated by reference in its entirety. Accordingly the use of deuterium-enriched ketamine, deuterium-enriched derivatives thereof and pharmaceutically acceptable salts thereof is contemplated and within the scope of the methods and compositions described herein. Deuterium can be incorporated in any position in replace of hydrogen synthetically, according to the synthetic procedures known in the art. For example, deuterium may be incorporated to various positions having an exchangeable proton, such as the amine N—H, via proton-deuterium equilibrium exchange. Thus, deuterium may be incorporated selectively or non-selectively through methods known in the art to provide deuterium enriched ketamine or norketamine.

In embodiments, ketamine or norketamine may be deuterated with one deuterium atom. In embodiments, ketamine or norketamine may be deuterated with two deuterium atoms. In embodiments, ketamine or norketamine may be deuterated with three deuterium atoms. In embodiments, ketamine or norketamine may be deuterated with more than three deuterium atoms.

Deuterium enriched ketamine or norketamine may be described by the percentage of incorporation of deuterium at a given position in the molecule in the place of hydrogen. For example, deuterium enrichment of 1% at a given position means that 1% of molecules in a given sample contain deuterium at that specified position. The deuterium enrichment can be determined using conventional analytical methods, such as mass spectrometry and nuclear magnetic resonance spectroscopy. In embodiments, deuterium enriched ketamine or norketamine means that the specified position is enriched with deuterium above the naturally occurring distribution (i.e., above about 0.0156%). In embodiments, deuterium enrichment is, e.g., no less than about 1%, no less than about 5%, no less than about 10%, no less than about 20%, no less than about 50%, no less than about 70%, no less than about 80%, no less than about 90%, or no less than about 98% of deuterium at a specified position. In embodiments, deuterium enrichment may be defined as, e.g., more than about 60%, more than about 65%, more than about 75%, more than about 80%, more than about 85%, more than about 95% deuterium at a specified position.

In embodiments, any position designated as being deuterium has a minimum deuterium incorporation of at least about 45% (e.g., at least about 52.5%, at least about 60%, at least about 67.5%, at least about 75%, at least about 82.5%, at least about 90%, at least about 95%, at least about 97%, at least about 99%, or at least about 99.5%) at the designated position(s). Thus, in embodiments, a composition including, e.g., a compound of formula (I) includes a distribution of isotopologues of the compound, provided at least about 45% of the isotopologues include a D at the designated position(s). In embodiments, at least about 90%, about 95%, about 97%, about 98%, about 98.5%, about 99%, about 99.5% or about 99.9% or greater of the isotopologues include a D at the designated position(s). In embodiments, a compound may be "substantially free" of other isotopologues of the compound. For example, less than about 50%, less than about 25%, less than about 10%, less than about 5%, less than about 2%, less than about 1%, or less than about 0.5% of other isotopologues are present. The term "isotopologue" refers to a species that has the same chemical structure and formula as a specific compound herein, with the exception of the isotopic composition at one or more positions, e.g., H vs. D. Thus an isotopologue differs from a specific compound herein in the isotopic composition thereof.

In embodiments, a ketamine derivative may be a compound of formula (1-A) having the following structure:

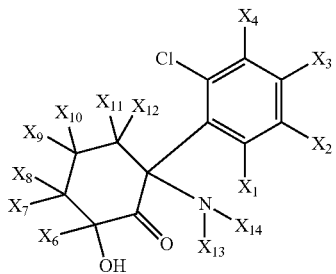

(I-A)

or a pharmaceutically acceptable salt thereof,
wherein $X_1$, $X_2$, $X_3$, $X_4$, $X_6$, $X_7$, $X_8$, $X_9$, $X_{10}$, $X_{11}$, $X_{12}$, $X_{13}$, and $X_{14}$ are each independently selected from the group consisting of hydrogen and deuterium, and wherein at least one of $X_1$, $X_2$, $X_3$, $X_4$, $X_6$, $X_7$, $X_8$, $X_9$, $X_{10}$, $X_{11}$, $X_{12}$, $X_{13}$, and $X_{14}$ is deuterium.

In embodiments of formula (I-A), when each of $X_1$, $X_2$, $X_3$, and $X_4$ is deuterium, then at least one of $X_6$, $X_7$, $X_8$, $X_9$, $X_{10}$, $X_{11}$, $X_{12}$, $X_{13}$, and $X_{14}$ is deuterium. In embodiments of formula (I-A), at least one of $X_6$, $X_7$, $X_8$, $X_9$, $X_{10}$, $X_{11}$, and $X_{12}$ is deuterium. In embodiments of formula (I-A), $X_6$, $X_7$, $X_8$, $X_9$, $X_{10}$, $X_{11}$, and $X_{12}$ are deuterium. In embodiments, $X_{13}$, and $X_{14}$ are deuterium. In embodiments of formula (I-A), $X_6$ is deuterium, $X_7$ and $X_8$ are deuterium, $X_9$ and $X_{10}$ are deuterium, and/or $X_{11}$ and $X_{12}$ are deuterium. In embodiments of formula (I-A), $X_6$ is deuterium. In embodiments of formula (I-A), $X_7$ and $X_8$ are hydrogen, $X_9$ and $X_{10}$ are hydrogen, and/or $X_{11}$ and $X_{12}$ are hydrogen. In embodiments, each of $X_7$, $X_8$, $X_9$, $X_{10}$, $X_{11}$, $X_{12}$, $X_{13}$, and $X_{14}$ is hydrogen. In embodiments of formula (I-A), $X_6$, $X_7$, and $X_8$ are deuterium. In embodiments of formula (I-A), $X_6$, $X_7$, and $X_8$ are hydrogen.

In embodiments, a ketamine derivative may be a compound of formula (1-B) having the following structure:

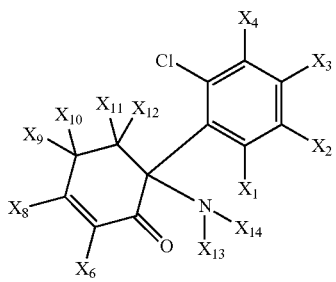

(I-B)

or a pharmaceutically acceptable salt thereof,
wherein $X_1$, $X_2$, $X_3$, $X_4$, $X_6$, $X_8$, $X_9$, $X_{10}$, $X_{11}$, $X_{12}$, $X_{13}$, and $X_{14}$ are each independently selected from the group consisting of hydrogen and deuterium, and wherein at least one of $X_1$, $X_2$, $X_3$, $X_4$, $X_6$, $X_8$, $X_9$, $X_{10}$, $X_{11}$, $X_{12}$, $X_{13}$, and $X_{14}$ is deuterium.

In embodiments of formula (I-B), when each of $X_1$, $X_2$, $X_3$, and $X_4$ is deuterium, then at least one of $X_6$, $X_8$, $X_9$, $X_{10}$, $X_{11}$, $X_{12}$, $X_{13}$, and $X_{14}$ is deuterium. In embodiments of formula (I-B), at least one of $X_6$, $X_8$, $X_9$, $X_{10}$, $X_{11}$, and $X_{12}$ is deuterium. In embodiments of formula (I-B), $X_6$, $X_8$, $X_9$, $X_{10}$, $X_{11}$, and $X_{12}$ are deuterium. In embodiments, $X_{13}$, and $X_{14}$ are deuterium. In embodiments of formula (I-B), $X_6$ is deuterium, $X_8$, $X_9$ and $X_{10}$ are deuterium, and/or $X_{11}$ and $X_{12}$ are deuterium. In embodiments of formula (I-B), $X_6$ is deuterium. In embodiments of formula (I-B), $X_8$, $X_9$ and $X_{10}$ are hydrogen, and/or $X_{11}$ and $X_{12}$ are hydrogen. In embodiments, each of $X_5$, $X_9$, $X_{10}$, $X_{11}$, $X_{12}$, $X_{13}$, and $X_{14}$ is hydrogen. In embodiments of formula (I-B), $X_6$ and $X_8$ are deuterium. In embodiments of formula (I-B), $X_6$ and $X_8$ are hydrogen.

In embodiments of formula (1-A) and/or (1-B), $X_1$, $X_2$, $X_3$, and $X_4$ are deuterium. In embodiments of formula (1-A) and/or (1-B), $X_1$, $X_2$, $X_3$, and $X_4$ are hydrogen. In embodiments of formula (1-A) and/or (1-B), $X_{13}$ and $X_{14}$ are deuterium. In embodiments of formula (1-A) and/or (1-B), $X_{13}$ and $X_{14}$ are hydrogen.

Exemplary compounds according to formula (I), (I-A), and (I-B) are provided in Tables A-D below.

TABLE A

Exemplary Compounds of Formula (I)

TABLE A-continued
Exemplary Compounds of Formula (I)
17
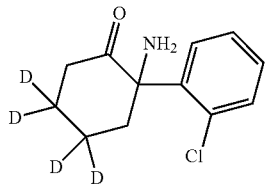 [SMILES: [2H]C1([2H])CC(=O)C(N)(c2ccccc2Cl)CC1([2H])[2H]]
18
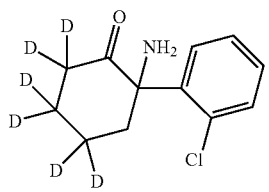 [SMILES: [2H]C1([2H])CC(N)(c2ccccc2Cl)C(=O)C([2H])([2H])C1([2H])[2H]]
19
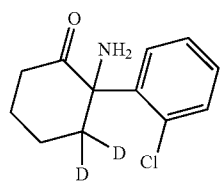 [SMILES: [2H]C1([2H])CCCC(=O)C1(N)c1ccccc1Cl]
20
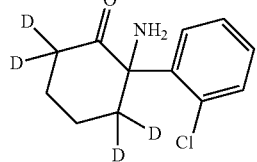
21
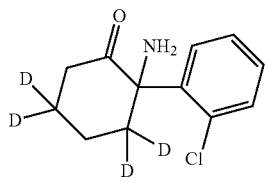 [SMILES: [2H]C1([2H])CC(=O)C(N)(c2ccccc2Cl)C([2H])([2H])C1]
22
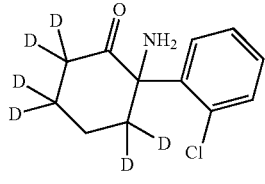 [SMILES: [2H]C1([2H])CC([2H])([2H])C(N)(c2ccccc2Cl)C(=O)C1([2H])[2H]]
23
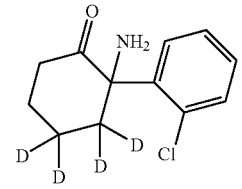 [SMILES: [2H]C1([2H])CCC(=O)C(N)(c2ccccc2Cl)C1([2H])[2H]]
24
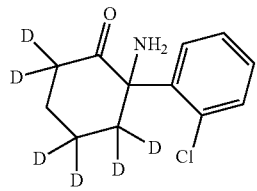 [SMILES: [2H]C1([2H])CC([2H])([2H])C([2H])([2H])C(N)(c2ccccc2Cl)C1=O]
TABLE A-continued
Exemplary Compounds of Formula (I)
25
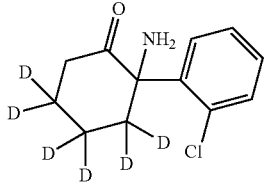 [SMILES: [2H]C1([2H])CC(=O)C(N)(c2ccccc2Cl)C([2H])([2H])C1([2H])[2H]]
26
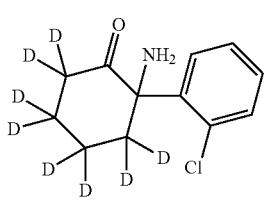 [SMILES: [2H]C1([2H])C(=O)C(N)(c2ccccc2Cl)C([2H])([2H])C([2H])([2H])C1([2H])[2H]]
TABLE B
Exemplary Compounds of Formula (I)
27
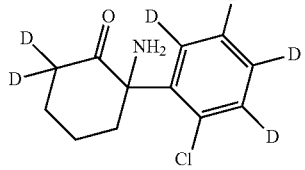
28
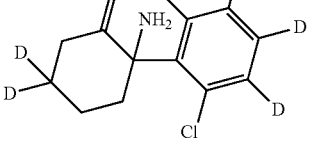
29
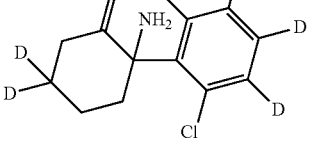
30
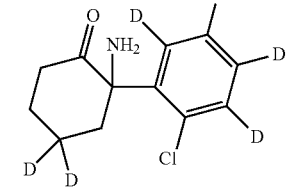
31
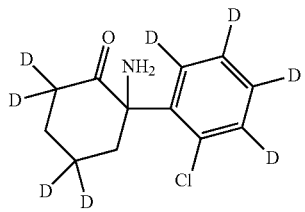 [SMILES: [2H]c1c([2H])c([2H])c(C2(N)CC([2H])([2H])CC([2H])([2H])C2=O)c(Cl)c1[2H]]

TABLE B-continued
Exemplary Compounds of Formula (I)
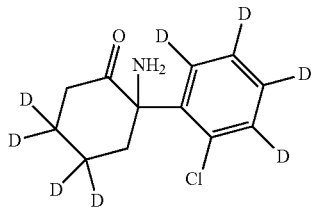 [SMILES: [2H]c1c([2H])c([2H])c(C2(N)CC([2H])([2H])C([2H])([2H])CC2=O)c(Cl)c1[2H]]
32
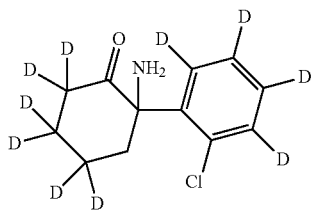 [SMILES: [2H]c1c([2H])c([2H])c(C2(N)CC([2H])([2H])C([2H])([2H])C([2H])([2H])C2=O)c(Cl)c1[2H]]
33
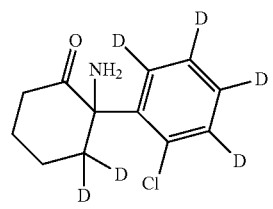 [SMILES: [2H]c1c([2H])c([2H])c(C2(N)C(=O)CCCC2([2H])[2H])c(Cl)c1[2H]]
34
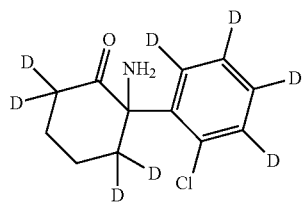 [SMILES: [2H]c1c([2H])c([2H])c(C2(N)C(=O)C([2H])([2H])CCC2([2H])[2H])c(Cl)c1[2H]]
35
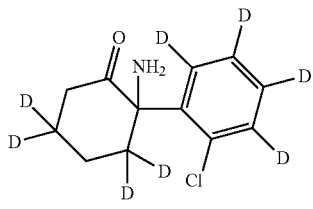 [SMILES: [2H]c1c([2H])c([2H])c(C2(N)C(=O)CC([2H])([2H])CC2([2H])[2H])c(Cl)c1[2H]]
36
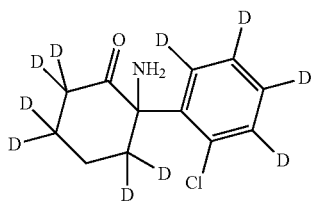 [SMILES: [2H]c1c([2H])c([2H])c(C2(N)C(=O)C([2H])([2H])C([2H])([2H])CC2([2H])[2H])c(Cl)c1[2H]]
37
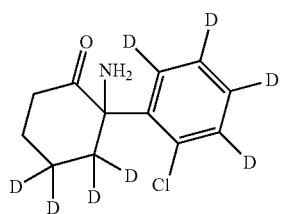 [SMILES: [2H]c1c([2H])c([2H])c(C2(N)C(=O)CCC([2H])([2H])C2([2H])[2H])c(Cl)c1[2H]]
38
TABLE B-continued
Exemplary Compounds of Formula (I)
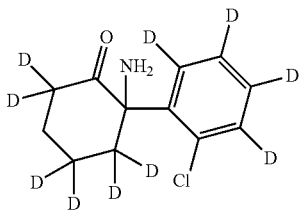 [SMILES: [2H]c1c([2H])c([2H])c(C2(N)C(=O)C([2H])([2H])CC([2H])([2H])C2([2H])[2H])c(Cl)c1[2H]]
39
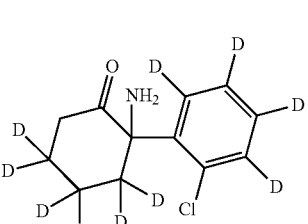
40
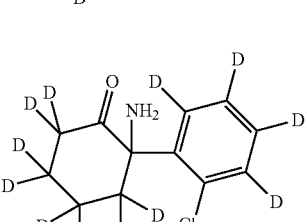
41
TABLE C
Exemplary Compounds of Formula (I-A)
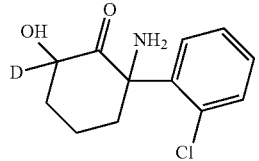 [SMILES: [2H]C1(O)CCCC(N)(c2ccccc2Cl)C1=O]
42
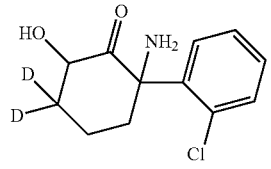 [SMILES: [2H]C1([2H])CCC(N)(c2ccccc2Cl)C(=O)C1O]
43
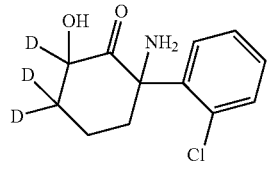 [SMILES: [2H]C1([2H])CCC(N)(c2ccccc2Cl)C(=O)C1([2H])O]
44
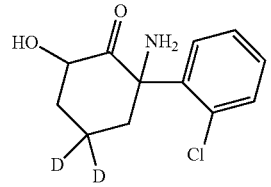 [SMILES: [2H]C1([2H])CC(O)C(=O)C(N)(c2ccccc2Cl)C1]
45

TABLE C-continued

Exemplary Compounds of Formula (I-A)

TABLE C-continued

Exemplary Compounds of Formula (I-A)

| # | Structure |
|---|---|
| 61 | (deuterated hydroxynorketamine analog) |
| 62 | (deuterated hydroxynorketamine analog) |
| 63 | (deuterated hydroxynorketamine analog) |
| 64 | (deuterated hydroxynorketamine analog) |
| 65 | (deuterated hydroxynorketamine analog) |
| 66 | (deuterated hydroxynorketamine analog) |
| 67 | (deuterated hydroxynorketamine analog) |
| 68 | (deuterated hydroxynorketamine analog) |
| 69 | (deuterated hydroxynorketamine analog) |
| 70 | (deuterated hydroxynorketamine analog) |
| 71 | (deuterated hydroxynorketamine analog) |

TABLE D

Exemplar Compounds of Formula (I-B)

| # | Structure |
|---|---|
| 72 | (deuterated dehydronorketamine analog) |
| 73 | (deuterated dehydronorketamine analog) |
| 74 | (deuterated dehydronorketamine analog) |

TABLE D-continued
Exemplar Compounds of Formula (I-B)
75
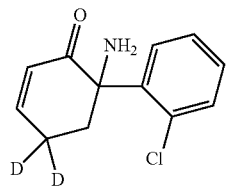 [SMILES: [2H]C1([2H])C=CC(=O)C(N)(c2ccccc2Cl)C1]
76
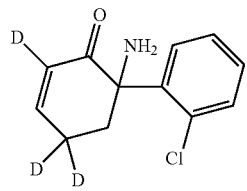 [SMILES: [2H]C1=CC([2H])([2H])CC(N)(c2ccccc2Cl)C1=O]
77
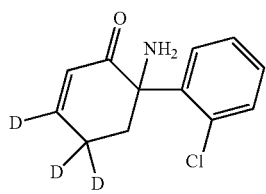 [SMILES: [2H]C1=CC(=O)C(N)(c2ccccc2Cl)CC1([2H])[2H]]
78
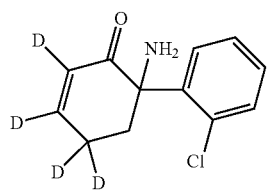 [SMILES: [2H]C1=C([2H])C([2H])([2H])CC(N)(c2ccccc2Cl)C1=O]
79
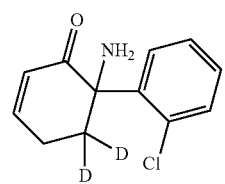 [SMILES: [2H]C1([2H])CC=CC(=O)C1(N)c1ccccc1Cl]
80
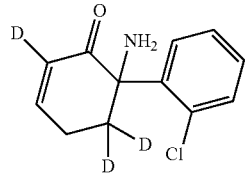 [SMILES: [2H]C1=CCC([2H])([2H])C(N)(c2ccccc2Cl)C1=O]
81
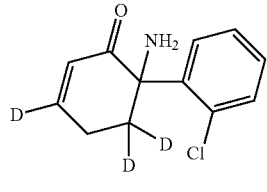 [SMILES: [2H]C1=CC(=O)C(N)(c2ccccc2Cl)C([2H])([2H])C1]
82
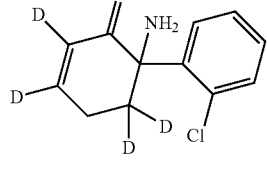
TABLE D-continued
Exemplar Compounds of Formula (I-B)
83
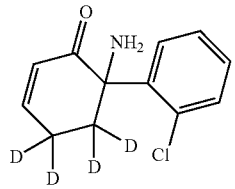 [SMILES: [2H]C1([2H])C=CC(=O)C(N)(c2ccccc2Cl)C1([2H])[2H]]
84
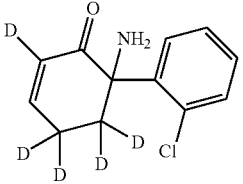 [SMILES: [2H]C1=CC([2H])([2H])C([2H])([2H])C(N)(c2ccccc2Cl)C1=O]
85
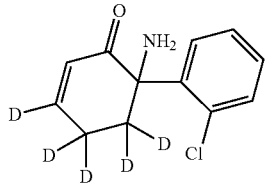 [SMILES: [2H]C1=CC(=O)C(N)(c2ccccc2Cl)C([2H])([2H])C1([2H])[2H]]
86
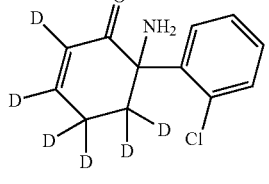
87
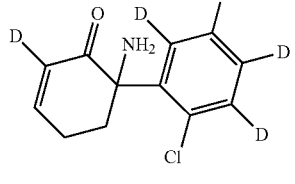
88
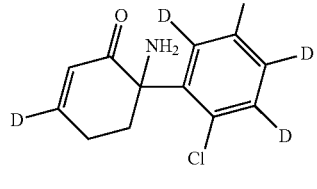
89
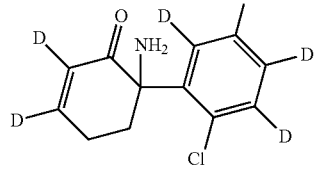
90
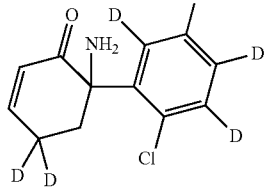

TABLE D-continued

Exemplar Compounds of Formula (I-B)

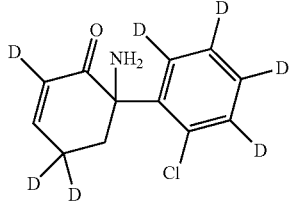 [SMILES: [2H]C1=CC([2H])([2H])CC(N)(c2c([2H])c([2H])c([2H])c([2H])c2Cl)C1=O]
91

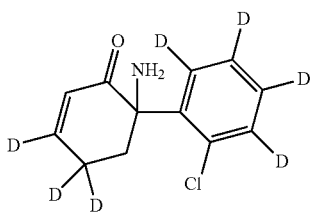 [SMILES: [2H]C1=CC(=O)C(N)(c2c([2H])c([2H])c([2H])c([2H])c2Cl)CC1([2H])[2H]]
92

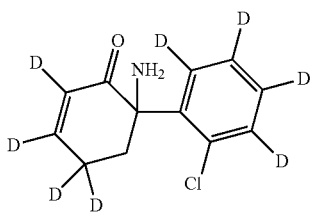 [SMILES: [2H]C1=C([2H])C([2H])([2H])CC(N)(c2c([2H])c([2H])c([2H])c([2H])c2Cl)C1=O]
93

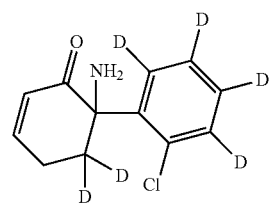 [SMILES: [2H]c1c([2H])c([2H])c(C2(N)C(=O)C=CCC2([2H])[2H])c(Cl)c1[2H]]
94

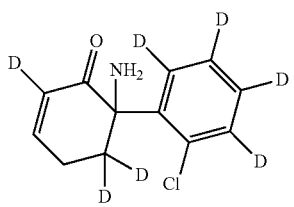 [SMILES: [2H]C1=CCC([2H])([2H])C(N)(c2c([2H])c([2H])c([2H])c([2H])c2Cl)C1=O]
95

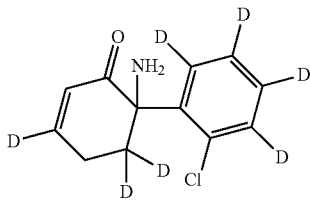 [SMILES: [2H]C1=CC(=O)C(N)(c2c([2H])c([2H])c([2H])c([2H])c2Cl)C([2H])([2H])C1]
96

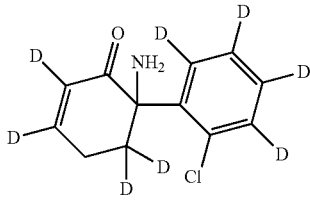 [SMILES: [2H]C1=C([2H])C(=O)C(N)(c2c([2H])c([2H])c([2H])c([2H])c2Cl)C([2H])([2H])C1]
97

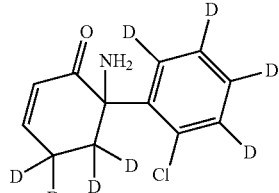
98

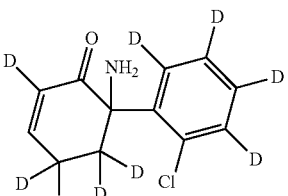
99

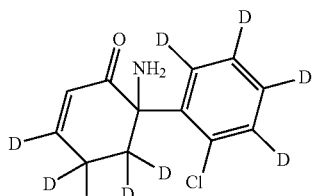
100

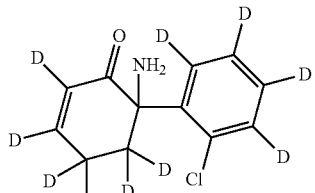
101

Ketamine, ketamine derivatives, analogues and structurally related compounds thereof useful in the disclosed methods include any form of the compounds, such as the base (zwitter ion), pharmaceutically acceptable salts, e.g., pharmaceutically acceptable acid addition salts, hydrates or solvates of the base or salt, as well as anhydrates, and also amorphous, or crystalline forms. "Pharmaceutically acceptable salts" of ketamine, norketamine, and other derivatives of ketamine include salts of the active compounds that are prepared with relatively nontoxic acids or bases, depending on the particular substituents found on the compounds described herein. When compounds herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts. Thus, the compounds herein may exist as salts, such as with pharmaceutically acceptable acids. Non-limiting examples of such salts include hydrochlorides, hydrobromides, phosphates, sulfates, methanesulfonates, nitrates, maleates, acetates, citrates, fumarates, propionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art. The neutral forms of the compounds may be regenerated by contacting the salt with a base or acid and isolating the parent compound in the conventional manner. The parent form of the compound may differ from the various salt forms in certain physical properties, such as solubility in polar solvents.

In embodiments, ketamine, norketamine, and/or other derivatives of ketamine, or a pharmaceutically acceptable salt of any of the foregoing, may include the racemic mixture, as well as compositions including each enantiomer individually. The compositions and methods contemplated herein may provide reduced dosing frequency, reduced adverse events and/or increased efficacy compared to a racemic mixture of ketamine, norketamine, and/or other derivatives of ketamine or pharmaceutically acceptable salts of any of the foregoing. In embodiments, compositions and methods that include each enantiomer individually may provide reduced dosing frequency, reduced adverse events and/or increased efficacy compared to the minor enantiomer. Thus, for example, contemplated herein are compositions and methods of treatment that provide the S enantiomer of ketamine, norketamine, or other derivatives of ketamine, or a pharmaceutically acceptable salt of any of the foregoing that is substantially free of the R enantiomer. In embodiments, methods and compositions herein include the R enantiomer of ketamine, norketamine, or other derivatives of ketamine, or a pharmaceutically acceptable salt of any of the foregoing substantially free of the S enantiomer. By "substantially free" it is meant that the composition includes less than 50% of the minor enantiomer. In embodiments, the compositions and methods herein may include less than about, e.g., 25%, 15%, 10%, 8%, 5%, 3%, 2%, or less than 1% of the minor enantiomer.

In embodiments, ketamine, norketamine, and/or other derivatives of ketamine, or a pharmaceutically acceptable salt of any of the foregoing, is administered at dosages ranging from about 0.1 mg/kg and about 10 mg/kg of body weight of a patient in need thereof, e.g., from about 0.1 mg/kg to 5.0 mg/kg at least once a day. For example, dosages may include amounts of ketamine, norketamine, and/or other derivatives of ketamine, or a pharmaceutically acceptable salt of any of the foregoing in the range of about, e.g., 1 mg to 500 mg, 1 mg to 250 mg, 1 mg to 100 mg, 1 mg to 30 mg, 1 mg to 20 mg, 1 mg to 15 mg, 0.1 mg to 10 mg, 0.1 mg to 15 mg, 0.1 mg to 20 mg, 0.1 mg to 30 mg, 0.1 mg to 40 mg, 0.1 mg to 50 mg, 0.1 mg to 60 mg, 0.1 mg to 70 mg, 0.1 mg to 80 mg, 0.1 mg to 90 mg, 0.1 mg to 100 mg, 0.15 mg to 12.5 mg, or 0.2 mg to 10 mg, with doses of 0.1 mg, 0.2 mg, 0.3 mg, 0.4 mg, 0.5 mg, 0.6 mg, 0.7 mg, 0.8 mg, 0.9 mg, 1.5 mg, 1.0 mg, 1.75 mg, 2 mg, 2.5 mg, 2.75 mg, 3 mg, 3.5 mg, 3.75 mg, 4 mg, 4.5 mg, 4.75 mg, 5 mg, 5.5 mg, 6 mg, 6.5 mg, 7 mg, 7.5 mg, 8 mg, 8.5 mg, 9 mg, 10 mg, 11 mg, 12 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, and 500 mg being specific examples of doses.

Typically, dosages of ketamine, norketamine, and/or other derivatives of ketamine, or a pharmaceutically acceptable salt of any of the foregoing are administered once, twice, thrice or four times daily to a patient in need thereof. The methods and compositions described herein may provide reduced dosing frequency and reduced adverse events and/or increased efficacy. In embodiments, ketamine, norketamine, and/or other derivatives of ketamine, or a pharmaceutically acceptable salt of any of the foregoing may be administered once weekly or twice weekly. In embodiments, the dosage may be about, e.g., 0.1-20 mg/day, or 0.2-15 mg/day, or 0.5-10 mg/day, or 0.75-5 mg/day, 1-300 mg/day, 1-200 mg/day, 5-100 mg/day, 10-100 mg/day for example 0.2 mg/day, 0.5 mg/day, 0.75 mg/day, 1 mg/day, 1.5 mg/day, 2 mg/day, 3 mg/day, 4 mg/day, 5 mg/day, 6 mg/day, 7 mg/day, 8 mg/day, 9 mg/day, 10 mg/day, 11 mg/day, 12 mg/day, 15 mg/day, 20 mg/day, 25 mg/day, 30 mg/day, 35 mg/day, 40 mg/day, 45 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 110 mg/day, 120 mg/day, 130 mg/day, 140 mg/day, 150 mg/day, 160 mg/day, 170 mg/day, 180 mg/day, 190 mg/day, 200 mg/day, 210 mg/day, 220 mg/day, 230 m/day, 240 mg/day, 250 mg/day, 260 mg/day, 270 mg/day, 280 mg/day, 290 m/day, 300 mg/day, 310 mg/day, 320 mg/day, 330 m/day, 340 mg/day, 350 mg/day, 360 mg/day, 370 mg/day, 380 mg/day, 390 m/day, or 400 mg/day. In embodiments, ketamine, norketamine, and/or other derivatives of ketamine, or a pharmaceutically acceptable salt of any of the foregoing is administered at doses of e.g., 0.2 mg to 1 mg in infants, 0.5 mg to 50 mg in children, or 1 mg to 300 mg in adults, once, twice, thrice or four times daily. It should be understood that these doses are exemplary and that those skilled in the art can adjust the doses upwardly or downwardly based on specific requirements of particular situations.

Methods of treating developmental encephalopathies by administering to a subject in need thereof an effective amount of ketamine, norketamine, and/or other derivatives of ketamine, or a pharmaceutically acceptable salt of any of the foregoing, are provided. An effective amount or therapeutically effective amount can be a dosage sufficient to treat, inhibit, or alleviate one or more symptoms of a developmental encephalopathy such as reducing the frequency or severity of seizures, reducing behavior abnormalities (or otherwise improving behavior); improving movement and balance issues, orthopedic conditions, alleviating delayed language and speech issues, improving growth and nutrition issues, reducing sleeping difficulties, chronic infections, alleviating sensory integration disorders, and disruptions of the autonomic nervous system; or to provide a desired pharmacologic and/or physiologic effect, for example, reducing, inhibiting, or reversing one or more of the underlying pathophysiological mechanisms underlying the neurological dysfunction, increasing dopamine levels or signaling, or a combination thereof. The precise dosage will vary according to a variety of factors such as subject-dependent variables (e.g., age, immune system health, clinical symptoms etc.).

In embodiments, the methods described herein are effective to reduce, delay, or prevent one or more other clinical symptoms of a developmental encephalopathy, e.g., Dravet syndrome. For example, the effect of a composition including ketamine, norketamine, and/or other derivatives of ketamine, or a pharmaceutically acceptable salt of any of the foregoing on a particular symptom, pharmacologic, or physiologic indicator can be compared to an untreated subject, or the condition of the subject prior to treatment. In embodiments, the symptom, pharmacologic, and/or physiologic indicator is measured in a subject prior to treatment, and again one or more times after treatment is initiated. In embodiments, the control is a reference level, or average determined based on measuring the symptom, pharmacologic, or physiologic indicator in one or more subjects that do not have the disease or condition to be treated (e.g., healthy subjects). In embodiments, the effect of the treatment is compared to a conventional treatment that is known the art.

As mentioned previously, chronic administration of ketamine has been associated with cognitive impairment. Accordingly, the methods and compositions described herein may surprisingly reduce cognitive impairment and provide, e.g., an increase in executive functioning in a patient diagnosed with a developmental encephalopathy such as Dravet syndrome.

In embodiments, compositions and methods of treatment are provided with low dosages of ketamine, norketamine, and/or other derivatives of ketamine, or a pharmaceutically acceptable salt of any of the foregoing such that the patient is provided one or more beneficial effects related to treatment of a developmental encephalopathy, such as, reduced fatigue, increased mood, increased concentration, increased behavioral control and/or increased cognitive ability. Ketamine and norketamine are known to have a relatively short half-life that may lead to the need for frequent dosing. Provided herein are dosage forms and dosing regimens that allow effective treatment of a developmental encephalopathies with potentially limited or substantially few negative side effects. Accordingly, the methods described herein may provide treatment of a developmental encephalopathy that may be considered surprising and unexpected.

It is believed that the disclosed compounds, such as ketamine, norketamine, and/or other derivatives of ketamine, or a pharmaceutically acceptable salt of any of the foregoing, can be used as a monotherapy as the only active agent. In embodiments, methods are provided of treating development encephalopathies using ketamine, norketamine, and/or other derivatives of ketamine, or a pharmaceutically acceptable salt of any of the foregoing, in a pharmaceutically acceptable carrier. In embodiments, methods of treating development encephalopathies include administration of ketamine, norketamine, and/or other derivatives of ketamine, or a pharmaceutically acceptable salt of any of the foregoing, in combination with one or more other active compounds. The combination therapies can include administration of the active agents together in the same admixture, or in separate admixtures. In embodiments, the pharmaceutical composition includes two, three, or more active agents. In embodiments, the combinations result in a more than additive effect on the treatment of the disease or disorder. Thus, treatment is provided of a developmental encephalopathy with a combination of agents that combined, may provide a synergistic effect that enhances efficacy.

Ketamine, norketamine, and/or other derivatives of ketamine, or a pharmaceutically acceptable salt of any of the foregoing may be formulated into pharmaceutical compositions for administration to a patient or subject. "Patient" and "subject" are used interchangeably herein and may include humans and non-humans. In embodiments, ketamine, norketamine, and/or other derivatives of ketamine, or a pharmaceutically acceptable salt of any of the foregoing may be formulated into pharmaceutical compositions suitable for oral (conventional release, immediate release and modified-release), parenteral, topical, rectal, vaginal, intranasal, inhalation or liquid administration, such as oral dosage forms like pills (e.g., tablets, capsules, caplets, troaches, lozenges, caches, gelcaps, caps, pellets, boluses, pastilles, orally disintegrating tablets, sublingual tablets and buccal tablets), thin films, powders, granules, crystals, liquid solutions, syrups, emulsions and suspensions, topical dosage forms like pastes, creams, ointments, gels, liquids, sprays, skin patches, dermal patches, balms, salves and implants, ophthalmic and otic dosage forms, e.g., drops, suspensions, emulsions, creams and gels, vaginal rings and inserts, suppositories, inhalation dosage forms like aerosols, inhalers, nebulizers and vaporizers, and parenteral dosage forms like intradermal (ID), intramuscular (IM), intraosseous (10), intraperitoneal (IP), intravenous (IV), caudal, intrathecal (ITH), subcutaneous (SC), and the like.

Pharmaceutical compositions herein may be provided with conventional release or modified release profiles. Modified release profiles include immediate release, delayed release, sustained release aka extended release, or other modified release profiles. In embodiments, pharmaceutical compositions with different drug release profiles may be combined to create a two phase or three-phase release profile. For example, pharmaceutical compositions may be provided with an immediate release and an extended release profile. In embodiments, pharmaceutical compositions may be provided with an extended release and delayed release profile. Such compositions may be provided as pulsatile formulations, multilayer tablets, or capsules containing tablets, beads, granules, etc. Compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, glidants, lubricants, disintegrants, fillers, and coating compositions. Tablets, capsules, suppositories and the like may be formed e.g., by direct-compression, wet-granulation, dry-granulation or by techniques involving molds and solidification. Those skilled in the art are familiar with techniques used in compounding conventional release, immediate release, delayed release, extended release, or other modified release dosage forms.

In embodiments, the pharmaceutical compositions herein may be provided with conventional release, immediate release, delayed release, or extended release profiles. Conventional (or unmodified) release oral dosage forms such as tablets or capsules typically release medications into the stomach or intestines as the tablet or capsule shell dissolves. The pattern of drug release from modified release (MR) dosage forms is deliberately changed from that of a conventional dosage form to achieve a desired therapeutic objective and/or better patient compliance. Types of MR drug products include orally disintegrating dosage forms (ODDFs) which provide immediate release, extended or sustained release dosage forms, delayed release dosage forms (e.g., enteric coated), and pulsatile release dosage forms.

An ODDF is a solid dosage form containing a medicinal substance or active ingredient which disintegrates rapidly, usually within a matter of seconds when placed upon the tongue. The disintegration time for ODDFs generally range from one or two seconds to about a minute. ODDFs are designed to disintegrate or dissolve rapidly on contact with saliva. This mode of administration can be beneficial to people who may have problems swallowing tablets whether it be from physical infirmity or psychiatric in nature. Patients with developmental encephalopathies, e.g., Dravet syndrome, may exhibit such behavior. Examples of ODDFs include orally disintegrating tablets, capsules and rapidly dissolving films and wafers.

Sustained released (SR), otherwise referred to herein as extended release dosage forms (ERDFs), have extended release profiles and are those that may allow a reduction in dosing frequency as compared to that presented by a conventional dosage form, e.g., a solution or unmodified release dosage form. ERDFs provide a sustained duration of action of a drug. Suitable formulations which provide extended release profiles are well-known in the art. For example, coated slow release beads or granules ("beads" and "granules" are used interchangeably herein) in which, e.g., ketamine, norketamine, and/or other derivatives of ketamine, or a pharmaceutically acceptable salt of any of the foregoing, is applied to beads, e.g., confectioners nonpareil beads, and then coated with conventional release retarding materials such as waxes, enteric coatings and the like. In embodiments, beads can be formed in which the ketamine, norketamine, and/or other derivatives of ketamine, or a pharmaceutically acceptable salt of any of the foregoing, is mixed with a material to provide a mass from which the drug leaches out. In embodiments, the beads may be engineered to provide different rates of release by varying characteristics of the coating or mass, e.g., thickness, porosity, using different materials, etc. Beads having different rates of release may be combined into a single dosage form to provide variable and/or continuous release. The beads can be contained in capsules or compressed into tablets. In embodiments, ketamine, norketamine, and/or other derivatives of ketamine, or a pharmaceutically acceptable salt of any of the foregoing, extended release dosage forms incorporate a matrix system such as a dual hydrophilic polymer matrix system. In embodiments, ketamine, norketamine, and/or other derivatives of ketamine, or a pharmaceutically acceptable salt of any of the foregoing, for example, a hydrochloride salt, is combined with a drug release controlling polymer to form an "inner" phase, which is then incorporated as discrete particles into an "external" phase of a second polymer. After administration, fluid from the gastrointestinal (GI) tract enters the tablet, causing the polymers to hydrate and swell. Drug is released slowly from the dosage form by a process of diffusion through the gel matrix that is essentially independent of pH.

Certain controlled release dosage forms are described in US Publication No. 2017/003570, herein incorporated by reference in its entirety. In embodiments, a SR dosage form incorporates a matrix release system. For example, a matrix system can be swellable, non-swellable, erodible or non-erodible, and includes polymers, including synthetic polymers, and naturally occurring polymers and derivatives, such as polysaccharides and proteins. In embodiments, the dosage form includes a non-erodible matrix system. Ketamine, norketamine, and/or other derivatives of ketamine, or a pharmaceutically acceptable salt of any of the foregoing, can be dissolved or dispersed in an inert matrix and released primarily by diffusion through the inert matrix once administered.

Examples of suitable materials for forming a matrix include chitin, chitosan, dextran, and pullulan, gum agar, gum arabic, gum karaya, locust bean gum, gum tragacanth, carrageenans, gum ghatti, guar gum, xanthan gum, and scleroglucan, starches, such as dextrin and maltodextrin, hydrophilic colloids, such as pectin, phosphatides, such as lecithin, alginates, propylene glycol alginate, gelatin, collagen, and cellulosics, such as ethyl cellulose (EC), methylethyl cellulose (MEC), carboxymethyl cellulose (CMC), carboxymethyl ethylcellulose (CMEC), hydroxyethyl cellulose (HEC), hydroxypropyl cellulose (HPC), cellulose acetate (CA), cellulose propionate (CP), cellulose butyrate (CB), cellulose acetate butyrate (CAB), cellulose acetate phthalate (CAP), cellulose acetate trimellitate (CAT), hydroxypropyl methyl cellulose (HPMC), HPMCP, HPMCAS, hydroxypropyl methyl cellulose acetate trimellitate (HPMCAT), and ethylhydroxy ethylcellulose (EHEC), polyvinyl pyrrolidone, polyvinyl alcohol, polyvinyl acetate, fatty acid esters, polyacrylamide, polyacrylic acid, copolymers of ethacrylic acid or methacrylic acid (EUDRAGIT™), Rohm America, Inc., Piscataway, N.J.), poly(2-hydroxyethylmethacrylate), polylactides, copolymers of L-glutamic acid and ethyl-L-glutamate, degradable lactic acid-glycolic acid copolymers, poly-D-(-)-3-hydroxybutyric acid, and other acrylic acid derivatives, such as homopolymers and copolymers of butylmethacrylate, methylmethacrylate, ethylmethacrylate, ethyl acrylate, (2-dimethylaminoethyl)methacrylate, and (trimethylaminoethyl)methacrylate chloride. Additional examples include polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers; and fatty compounds, such as carnauba wax, microcrystalline wax, and triglycerides such as hydrogenated castor oil.

In embodiments, the matrix forming material can be present in the dosage form in a concentration of between 10 and 95 wt %, e.g., 15 to 85 wt %, 20 to 75 wt %, 25 to 65 wt %, or 30 to 60 wt %, based on the total weight of the dosage form. The dosage form including a matrix system may also include carriers such as lubricants, fillers, glidants, binders, and/or stabilizers. In embodiments, carriers may be present in amounts, e.g., 0 to 90 wt. %, 5 to 70 wt. %, 10 to 50 wt. %, or 15 to 30 wt. % fillers, optionally 0 to 25 wt. %, 1 to 20 wt. %, or 5 to 15 wt. % binders, 0 to 5 wt. %, 0.1 to 4 wt. %, or 0.5 to 3 wt. % glidants, 0 to 5 wt. %, 0.1 to 3 wt. %, or 0.3 to 2 wt. % lubricants based on the total weight of the dosage form.

Those skilled in the are familiar with techniques for preparing matrix sustained release dosage forms. For example, matrix sustained release dosage forms can be prepared by direct-compression, wet-granulation, dry-granulation or techniques involving molds.

In embodiments, dosage forms herein can incorporate an osmotic sustained release device, including e.g., one-chamber system (elementary osmotic pump), two-chamber system (push-pull systems), asymmetric membrane technology (AMT), or extruding core system (ECS). Osmotic sustained release devices may include cores, for example, tablets including ketamine, norketamine, and/or other derivatives of ketamine, or a pharmaceutically acceptable salt of any of the foregoing, which are surrounded by a semipermeable membrane which may have at least one orifice. In embodiments, the water-permeable membrane is impermeable to the components of the core but permits water to enter the system from outside by osmosis. As water penetrates in, osmotic pressure is produced, which causes release of the active ingredient in dissolved or suspended form through one or more orifice(s) in the membrane. The total active ingredient release and the release rate can be controlled via the thickness and porosity of the semipermeable membrane, the composition of the core and the number and size of the orifice(s).

In embodiments, osmotic agents that create osmotic pressure can be incorporated into an osmotic sustained release device. In, e.g., an osmotic two-chamber system, the core can consist of two layers, one active ingredient layer and one osmosis layer. The active ingredient layer can include 1 to 70% ketamine, norketamine, and/or other derivatives of ketamine, or a pharmaceutically acceptable salt of any of the foregoing, and 30 to 95% of one or more osmopolymers. The osmosis layer may include, e.g., 30 to 90% of one or more osmopolymers, 10 to 60% of an osmogen, where the difference from 100% in the individual layers is formed in each case independently of one another by one or more additional ingredients in the form of pharmaceutically acceptable carriers.

In embodiments, osmotic agents are water-swellable polymers, which are also referred to as "osmopolymers" and "hydrogels," including hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly (acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

In embodiments, osmotic agents are osmogens which are capable of imbibing water to affect an osmotic pressure gradient across the barrier of a surrounding coating. Examples of osmogens include water-soluble salts of inorganic or organic acids or nonionic organic substances with a high solubility in water, such as, for example, carbohydrates such as sugars, sugar alcohols, or amino acids. In embodiments, osmogens can be inorganic salts such as chlorides, sulphates, carbonates and bicarbonates of alkali metals or alkaline earth metals, such as lithium, sodium, potassium, magnesium, calcium, and phosphates, hydrogen phosphates or dihydrogen phosphates, acetates, succinates, benzoates, citrates or ascorbates thereof. It is also possible to use pentoses such as arabinose, ribose or xylose, hexoses such as glucose, fructose, galactose or mannose, disaccharides such as sucrose, maltose or lactose or trisaccharides such as raffinose. Suitable water-soluble amino acids include glycine, leucine, alanine or methionine. Sodium chloride may be utilized as an osmogen. Osmogens can be present in an amount, e.g., of 10 to 30% based on the total mass of the core ingredients.

In embodiments, a combination of osmogens and osmopolymers can be used in a osmotic sustained release device. In embodiments, a core can include pharmaceutically acceptable carriers including buffers such as sodium bicarbonate, binders such as hydroxypropylcellulose, hydroxypropylmethyl cellulose and/or polyvinylpyrrolidone, lubricants such as magnesium stearate, wetting agents such as sodiumlauryl sulphate and/or flow regulators such as colloidal silicon dioxide.

In embodiments, materials for forming a semipermeable membrane of the osmotic sustained release device may include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. In embodiments, the material for forming the semipermeable membrane may be, e.g., plasticized, unplasticized, and reinforced cellulose acetate (CA), cellulose diacetate, cellulose triacetate, CA propionate, cellulose nitrate, cellulose acetate butyrate (CAB), CA ethyl carbamate, CA phthalate, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural and synthetic waxes. In embodiments, a semipermeable membrane may also be a hydrophobic microporous membrane which is permeable to water vapor. Hydrophobic polymers for forming hydrophobic but water-permeable membranes include polyalkenes, polyethylene, polypropylene, polytetrafluoro-ethylene, polyacrylic acid derivatives, polyethers, polysulfones, polyethersulfones, polystyrenes, polyvinyl halides, polyvinylidene fluoride, polyvinyl esters and ethers, and natural and synthetic waxes.

In embodiments, orifices functioning as delivery port(s) on a semipermeable membrane may be formed post-coating by, e.g., mechanical or laser drilling. Alternatively, delivery port(s) may be formed in situ by erosion of a plug of water-soluble material or by rupture of a thinner portion of the membrane over an indentation in the core. Yet further, delivery ports may be formed during the coating process, as in the case of asymmetric membrane coatings.

In embodiments, a dosage form herein can be an AMT sustained release dosage form, which includes an asymmetric osmotic membrane that coats a core including ketamine, norketamine, and/or other derivatives of ketamine, or a pharmaceutically acceptable salt of any of the foregoing, and other pharmaceutically acceptable carriers. AMT sustained release dosage forms can be prepared according to conventional methods and techniques known to those skilled in the art, including direct compression, dry granulation, wet granulation, or a dip-coating method.

In embodiments, a dosage form herein can be formulated as a ECS sustained release dosage form, which includes an osmotic membrane that coats a core including ketamine, norketamine, and/or other derivatives of ketamine, or a pharmaceutically acceptable salt of any of the foregoing, hydroxylethyl cellulose, and other pharmaceutically acceptable carriers.

In embodiments, an oral dosage form herein is a multi particulate dosage form and includes a multitude of particles. As used herein, "particles" is meant to encompass pellets, granules, spheroids, beads, and microtablets. For example, particles can be pellets which contain a core including ketamine, norketamine, and/or other derivatives of ketamine, or a pharmaceutically acceptable salt of any of the foregoing. Accordingly, particles, pellets, granules, spheroids, beads, and microtablets may be used interchangeably herein.

In embodiments, particles can contain a core including ketamine, norketamine, and/or other derivatives of ketamine, or a pharmaceutically acceptable salt of any of the foregoing, and a release control layer coated upon the core. In embodiments, the release control layer is (physically) separated from the ketamine, norketamine, and/or other derivatives of ketamine, or a pharmaceutically acceptable salt of any of the foregoing, containing core. The ketamine, norketamine, and/or other derivatives of ketamine, or a pharmaceutically acceptable salt of any of the foregoing, containing core may be a core which includes carriers. In embodiments, the carriers do not substantially retard or delay the release of the ketamine.

In embodiments, the core includes a layer of ketamine, norketamine, and/or other derivatives of ketamine, or a pharmaceutically acceptable salt of any of the foregoing, on an inert core. The inert core (also referred to as seed core or neutral bead) may be particles which are, e.g., spherical, and made, e.g., from sugar or cellulose or other suitable materials. By way of example, spherical inert cores based on saccharose, such as those commercially available under the trade name Suglets™ or those based on cellulose, such as those commercially available under the trade name Celphere™ or Cellets™ may be suitable. Inert cores may have a particle size, e.g., in the range of 100 to 500 µm, 200 to 400 µm, with the particle size range indicating the size range for 90% of the particles as determined by sieve analysis.

In embodiments, ketamine, norketamine, and/or other derivatives of ketamine, or a pharmaceutically acceptable salt of any of the foregoing, as an active agent, is provided by coating an active agent-containing layer directly onto the inert cores. In embodiments, the active agent-containing layer does not delay release of ketamine, i.e. is an immediate-release layer. In embodiments, each particle may contain a core including the active agent and a release control layer coated upon the core. In embodiments, particles containing active agent cores and a release control layer coated upon the cores can be mixed with other particles. As used herein, "active agent" includes ketamine, norketamine, and/or other derivatives of ketamine, or a pharmaceutically acceptable salt of any of the foregoing.

In embodiments, the core is not a neutral bead as described above, but a particle including active agent and optionally at least one pharmaceutically acceptable carrier. The active agent-containing particle can be formed, e.g., by dry granulation, wet granulation, spray granulation or extrusion.

In embodiments, a suitable active agent-containing core includes, e.g., 10 to 50 wt. %, 15 to 40 wt. %, 20 to 30 wt. % inert core (neutral bead), 20 to 90 wt. %, 35 to 80 wt. %, 50 to 70 wt. % active agent, e.g., ketamine hydrochloride, 0.1 to 20 wt. %, 1 to 15 wt. %, 3 to 10 wt. % binder, and optionally 0 to 20 wt. %, 1 to 15 wt. %, 3 to 10 wt. % glidant, based on the total weight of the active agent containing core.

In embodiments, binders may be used for the preparation of films, such as active agent containing layers, around an inert core. Exemplary binders include synthetic polymers, such as polyvinyl pyrrolidone (PVP), vinyl pyrrolidone-vinyl acetate-copolymer, modified celluloses, such as hydroxy alkyl celluloses and mixtures thereof. A binder may be used, e.g., in an amount of 0 to 25% by weight, e.g., 0.1 to 15% by weight, 1 to 10% by weight of the sustained release dosage form. In embodiments, hypromellose (HPMC) or PVP may be used as a binder in the active agent-containing core. In embodiments, HPMC has a methoxy content, e.g., of 20% to 40%, 25% to 35%. Further, HPMC may have a hydroxypropoxy content of, e.g., about 5% to 15%, 7% to 12%. In embodiments, a 2% by weight (aqueous) solution of said HPMC may have a viscosity of 0.5 to 100 mPas, 1 to 50 mPas, 2 to 10 mPas, measured at 20° C., measured, e.g., by using a Brookfield-Synchro-Lectric LVF viscosimeter. In embodiments, PVP may have an average molecular weight, e.g., of 1,000 to 2,500,000, 5,000 to 2,000,000, or 10,000 to 1,500,000.

In embodiments, glidants such as disperse silica, e.g., Aerosil™, or talc can be used in the active agent-containing core. In embodiments, the active agent containing core does not include a glidant.

In embodiments, a release control layer may be disposed in direct vicinity, i.e., in immediate contact with and surrounding the active agent containing core. In embodiments, an intermediate layer may be disposed between the active agent containing core and the release control layer. This intermediate layer may further control the release of active agent from the core. In embodiments, if present, the intermediate layer may not substantially influence the release from the core.

In embodiments, the release control layer includes a release control substance for controlling the release of active agent from the pellets. The release control substance may be any substance known in the art as suitable to control the release of an active substance. Examples of suitable control release substances include cellulose esters, such as cellulose acetate phthalate, polyvinyl pyrrolidone, polyvinyl alcohol, polyvinyl acetate, polyvinyl chloride, nylon, polyamide, polyethylene oxide, polylactide-co-glycolide and mixtures thereof. Further suitable polymers include those selected from alkylcelluloses, e.g., cellulose ethers, polymers and copolymers based on acrylate or methacrylate, polymers and copolymers based on acrylic or methacrylic esters and mixtures thereof. In embodiments, the release control substance may be a water insoluble polymer, e.g., an alkyl cellulose such as ethyl cellulose.

In embodiments, if the release control substance is a polymer, it can have a weight average molecular weight of, e.g., 5,000 to 500,0000 g/mol, 50,000 to 900,000 g/mol, 100,000 to 400,000 g/mol, e.g., 140,000 to 300,000 g/mol. The weight average molecular weight may be determined, e.g., by gel permeation chromatography. In embodiments, in addition or in the alternative to one or more of the properties mentioned above, the release control substance, e.g., a polymer, may have a solubility in water of less than, e.g., 20 mg/l, less than 15 mg/l, e.g., between 0.001 to 10.0 mg/l. In embodiments, in addition or in the alternative to one or more of the properties mentioned above, the polymer may have a glass transition temperature of 20 to 220° C., e.g., 60 to 150° C. or 90 to 140° C. The glass transition temperature may be measured, e.g., by differential scanning calorimetry DSC, using e.g., a Mettler Toledo instrument at a heating/cooling rate of, e.g., 10° C. per minute. In embodiments, the release-control substance may be ethylcellulose having an ethoxyl content of, e.g., about 30 to 70%, e.g., about 40 to 60%. In embodiments, a 2% by weight (aqueous) solution of ethylcellulose may have a viscosity of 5 to 500 mPas, e.g., 10 to 100 mPas, measured at 25° C., using, e.g., a Brookfield-Synchro-Lectric LVF viscosimeter.

In embodiments, the release control substance is contained in an amount of 0.1 to 80% by weight of the total weight of the particles containing active agent in the dosage form, e.g., in amounts of 0.5 to 60% by weight, 10 to 50% by weight, 15 to 40% by weight, of the total weight of the pellets in the dosage form. Control of the release rate can be adapted by appropriate selection of the control release substance or mixture of such substances, its/their amount, coating thickness, inclusion of further excipients/carriers, such as pore formers and/or plasticizers or others. In embodiments, one or more additional excipients/carriers may be used in the release control substance, e.g., in a release control layer. In embodiments, a polymeric release control substance may be a plasticizer and/or a pore former and/or glidants for use with the release control substance. In embodiments, a plasticizer is a substance that typically lowers the glass transition temperature of a polymer. It may be used in admixture with the polymer and lower the glass transition temperature by at least, e.g., 2° C., 3° C., 4° C., or at least 5° C., e.g., between 5 and 30° C., as compared to the polymer alone. In embodiments, the plasticizer may be triethyl citrate or propylene glycol.

In embodiments, a pore former may be is a substance having a water-solubility which is higher than the water solubility of the release-control substance. In embodiments, the pore former has a solubility in water of more than 20 mg/l, e.g., 50 mg/l to 5000 mg/l, 100 to 1000 mg/l. The solubility in water may be determined as described above. In embodiments, hydroxypropyl cellulose (HPC) is used as pore former.

As an example, the release control layer may include 20 to 95 wt. %, e.g., 40 to 80 wt. %, 50 to 70 wt. % release control substance, and as described above, 0.1 to 30 wt. %, e.g., 1 to 25 wt. %, 5 to 20 wt. % pore former, and as described above, 0.1 to 30 wt. %, e.g., 1 to 25 wt. %, 5 to 20 wt. % plasticizer, and optionally, as described above, 0 to 40 wt. %, e.g., 3 to 30 wt. %, 5 to 20 wt. % glidant, based on the total weight of the release control layer. The release control layer may be a single layer or a plurality of layers.

In embodiments, a sustained release dosage form is in the form of a tablet or a capsule. In embodiments, particles containing active agent are mixed into an "external phase" in order to be compressed into tablets. The external phase should ensure the stability of the particles containing active agent during the compression and may be composed of one or more pharmaceutically acceptable carriers, such as fillers, binders, disintegrants, glidants and lubricants.

Fillers may be used, e.g., to dilute a pharmaceutical composition and provide bulk. Examples for fillers include lactose, starch, calcium phosphate, calcium carbonate, saccharose, sugar alcohols such as mannitol, sorbitol, xylitol, and celluloses and derivatives such as microcrystalline cellulose. In embodiments, a filler mixture may include, e.g., sodium carboxymethyl cellulose and microcrystalline cellulose, in a weight ratio of, e.g., 5:1 to 1:5, e.g., 3:1 to 1:3. For example, a filler mixture may contain sodium carboxymethyl cellulose and microcrystalline cellulose, in a weight ratio of, e.g., 5:1 to 1:5, e.g., 3:1 to 1:3. A filler or mixture of fillers may be used in an amount of 0 to 80% by weight, e.g., 1 to 70% by weight, based on the total weight of the sustained release oral dosage form, e.g., a tablet.

Binders may be used, e.g., to enhance the integrity and stability of tablets. In addition, they may improve the suitability of pharmaceutical compositions for granulation. Binders may also used for the preparation of films, such as active agent containing layers, around an inert core. Exemplary binders include synthetic polymers, such as polyvinyl pyrrolidone, vinyl pyrrolidone-vinyl acetate-copolymer, modified celluloses, such as hydroxy alkyl celluloses and mixtures thereof. A binder may be used in an amount of, e.g., 0 to 30% by weight, e.g., 0.1 to 15% by weight, e.g., 1 to 10% by weight, of a sustained release oral dosage form. In embodiments, hypromellose (HPMC) may be used as binder.

Disintegrants may be used to enhance the disintegration of dosage forms, e.g., tablets, after immersion in water or gastric juices. Examples of disintegrants include carrageenan, starchs, croscarmellose, crospovidone and mixtures thereof. Disintegrants may be used in amounts of, e.g., 0 to 25% by weight, e.g., 1 to 20% by weight, e.g., 3 to 15% by weight of a sustained release oral dosage form, e.g., tablets.

Glidants, such as disperse silica, e.g., Aerosil™ or talc may be used, e.g., reduce friction among components of pharmaceutical dosage forms during manufacture. Glidants (or mixture thereof) may be used in an amount of, e.g., 0 to 5% by weight, e.g., 0.1 to 4% by weight of the sustained release oral dosage form, e.g., a tablet.

Lubricants, may be used to improve processing of pharmaceutical dosage forms, e.g., during compression of tablets. For example, lubricants may reduce friction at the interface between a tablets surface and a dye wall during ejection. Suitable lubricants include, e.g., stearic acid, magnesium stearate, adipic acid and sodium stearyl fumarate.

In embodiments, the amount of active agent containing particles in a sustained release dosage form may range from 1% to 100% by weight, based on the total weight of the sustained release dosage form. In embodiments, active agent containing particles may form 20% to 90% by weight, e.g., 25% to 80% by weight, of the sustained release dosage form based on the total weight.

In embodiments, an exemplary external phase (without coated cores) may include, e.g., 85 to 99.9%, e.g., 90 to 98% by weight filler, 0 to 5%, e.g., 0.1 to 1.0% by weight lubricant and 0.1 to 10%, e.g., 1.0 to 5% by weight glidant, based on the total weight of the external phase.

In embodiments, an oral dosage form herein, e.g., in the form of a tablet, may include an external film for improved ease of swallowing, for protection, for coloring, for taste-masking or other purposes. In embodiments, an external film does not influence the release of active agent to any significant extent. An external film may be made from well-known ingredients for this purpose. For example, a combination of hypromellose, talc, a coloring agent, e.g., titanium dioxide, and/or a polymer, e.g., polyethylene glycol. Ready to use products, e.g., Opadry™ based on hypromellose or polyvinyl alcohol may be used for the film coating. This optional film may or may not counted towards the total weight of the sustained release dosage form herein.

In embodiments, the ketamine salt may be ketamine hydrochloride. Sustained release dosage forms may contain ketamine, norketamine, and/or other derivatives of ketamine, or a pharmaceutically acceptable salt of any of the foregoing, in any of the amounts previously recited. For example, amounts of, e.g., 5 to 400 mg, or 5 to 200 mg. If ketamine, norketamine, and/or other derivatives of ketamine, are used as free base, the amount of 5 to 400 mg refers to the weight of the free base. If ketamine, norketamine, and/or other derivatives of ketamine, is used in the form of a pharmaceutical acceptable salt, the amount of 5 to 400 mg refers to the weight of the salt. By way of example, a SR dosage form can contain, e.g., 10 mg ketamine, 20 mg ketamine, 40 mg ketamine, 80 mg ketamine, 100 mg ketamine, 120 mg ketamine, 140 mg ketamine, 160 mg ketamine, 180 mg ketamine, 200 mg ketamine, 220 mg ketamine, 240 mg ketamine, 260 mg ketamine, 280 mg ketamine, 300 mg ketamine, 320 mg ketamine, 340 mg ketamine, 360 mg ketamine, 380 mg ketamine, 10 mg ketamine hydrochloride, 20 mg ketamine hydrochloride, 40 mg ketamine hydrochloride, 80 mg ketamine hydrochloride, 100 mg ketamine hydrochloride, 120 mg ketamine hydrochloride, 140 mg ketamine hydrochloride, 160 mg ketamine hydrochloride, 180 mg ketamine hydrochloride, 200 mg ketamine hydrochloride, 220 mg ketamine hydrochloride, 240 mg ketamine hydrochloride, 260 mg ketamine hydrochloride, 280 mg ketamine hydrochloride, 300 mg ketamine hydrochloride, 320 mg ketamine hydrochloride, 340 mg ketamine hydrochloride, 360 mg ketamine hydrochloride, 380 mg ketamine hydrochloride or 400 mg ketamine hydrochloride. By way of example, a SR dosage form can contain, e.g., 10 mg norketamine, 20 mg norketamine, 40 mg norketamine, 80 mg norketamine, 100 mg norketamine, 120 mg norketamine, 140 mg norketamine, 160 mg norketamine, 180 mg norketamine, 200 mg norketamine, 220 mg norketamine, 240 mg norketamine, 260 mg norketamine, 280 mg norketamine, 300 mg norketamine, 320 mg norketamine, 340 mg norketamine, 360 mg norketamine, 380 mg norketamine, 400 mg norketamine, 10 mg norketamine hydrochloride, 20 mg norketamine hydrochloride, 40 mg norketamine hydrochloride, 80 mg norketamine hydrochloride, 100 mg norketamine hydrochloride, 120 mg norketamine hydrochloride, 140 mg norketamine hydrochloride, 160 mg norketamine hydrochloride, 180 mg norketamine hydrochloride, 200 mg norketamine hydrochloride, 220 mg norketamine hydrochloride, 240 mg norketamine hydrochloride, 260 mg norketamine hydrochloride, 280 mg norketamine hydrochloride, 300 mg norketamine hydrochloride, 320 mg norketamine hydrochloride, 340 mg norketamine hydrochloride, 360 mg norketamine hydrochloride, 380 mg norketamine hydrochloride or 400 mg norketamine hydrochloride.

By way of example, a SR dosage form can include: i) ketamine-containing cores including 1 to 30 wt. %, e.g., 2 to 20 wt. %, or 3 to 10 wt. % inert cores, 1 to 40 wt. %, e.g., 5 to 20 wt. %, or 10 to 15 wt. %, ketamine or ketamine hydrochloride, 0.01 to 10 wt. %, e.g., 0.1 to 5 wt. %, or 0.5 to 3 wt. % binder, and 0 to 10 wt. %, e.g., 0.1 to 5 wt. %, e.g., 0.5 to 3 wt. % glidant, ii) a release-control layer coated on each ketamine-containing core, including 1 to 40 wt. %, e.g., 3 to 20 wt. %, e.g., 7 to 15 wt. % release-control substance, 0.01 to 10 wt. %, e.g., 0.1 to 6 wt. %, e.g., 1 to 4 wt. % pore former, 0 to 10 wt. %, e.g., 0.1 to 6 wt. %, e.g., 1 to 4 wt. % plasticizer, 0 to 15 wt. %, e.g., 0.1 to 10 wt. %, e.g., 0.5 to 5 wt. % glidant, and iii) an external phase including 20 to 85%, e.g., 40 to 75%, e.g., 50 to 65% filler, 0 to 3 wt. %, e.g., 0.001 to 2.0 wt. %, e.g., 0.1 to 0.5 wt. % lubricant and 0 to 5 wt. %, e.g., 0.1 to 5 wt. %, e.g., 0.5 to 2.0 wt. % glidant, wherein all wt. % are based on the total weight of the dosage form (without film coating).

In embodiments, SR tablets may have a hardness of 40 to 300 N, e.g., 50 to 200 N.

In embodiments, administration of a single oral dosage form leads in-vivo to a $C_{max}$ of ketamine of 1 to 150 ng/ml, e.g., 2 to 120 ng/ml, e.g., 3 to 100 ng/ml, e.g., 4 to 70 ng/ml, e.g., 5 to 40 ng/ml. In embodiments, administration of ketamine provides and in vivo plasma profile wherein $C_{max}$ is less than about 25 ng/ml, $C_{max}$ is less than about 25 ng/ml, $C_{max}$ is less than about 10 ng/ml, or $C_{max}$ is less than about 5 ng/ml. In embodiments, administration of a single oral dosage form leads in-vivo to a $AUC_{0-\infty}$ of ketamine of 5 to 1000 ng·hr/ml, e.g., 10 to 750 ng·hr/ml, e.g., 50 to 600 ng·hr/ml, e.g., 100 to 400 ng·hr/ml. In embodiments, administration of ketamine provides and in vivo plasma profile wherein a $AUC_{0-\infty}$ is less than about 200 ng·hr/ml, a $AUC_{0-\infty}$ is less than about 100 ng·hr/ml, a $AUC_{0-\infty}$ is less than about 50 ng·hr/ml, a $AUC_{0-\infty}$ is less than about 25 ng·hr/ml, or a $AUC_{0-\infty}$ is less than about 15 ng·hr/ml.

In embodiments, administration of a single oral dosage form leads in-vivo to a $C_{max}$ of norketamine of 5 to 750 ng/ml, e.g., 10 to 600 ng/ml, e.g., 15 to 500 ng/ml, e.g., 20 to 400 ng/ml, e.g., 25 to 300 ng/ml, and to a $AUC_{0-\infty}$ of 100 to 8000 ng·hr/ml, e.g., 150 to 6000 ng·hr/ml, e.g., 500 to 4000 ng·hr/ml.

In embodiments, $T_{max}$ of ketamine is 3 to 9 h, e.g., 3 to 8 h, e.g., 4 to 7 h, e.g., 5 to 7 h.

In embodiments, $T_{max}$ of norketamine is 3 to 9 h, e.g., 3 to 8 h, e.g., 4 to 7 h, e.g., 5 to 7 h.

In embodiments, an oral dosage form herein has a $F_{abs}$ of 5 to 25%, e.g., 7 to 20%, e.g., 9 to 18%.

In embodiments, modified dosage forms herein incorporate delayed release dosage forms having delayed release profiles. Delayed release dosage forms can include delayed release tablets or delayed release capsules. A delayed release tablet is a solid dosage form which releases a drug (or drugs) such as ketamine, norketamine, and/or other derivatives of ketamine, or a pharmaceutically acceptable salt of any of the foregoing, at a time other than promptly after administration. A delayed release capsule is a solid dosage form in which the drug is enclosed within either a hard or soft soluble container made from a suitable form of gelatin, and which releases a drug (or drugs) at a time other than promptly after administration. For example, enteric-coated tablets, capsules, particles and beads containing the active agent are well-known examples of delayed release dosage forms. Enteric coated tablets, capsules and particles and beads pass through the stomach and release the drug in the intestine. In embodiments, a delayed release tablet can be a solid dosage form containing a conglomerate of medicinal particles that releases a drug (or drugs) at a time other than promptly after administration. In embodiments, the conglomerate of medicinal particles are covered with a coating which delays release of the drug. In embodiments, a delayed release capsule is a solid dosage form containing a conglomerate of medicinal particles that releases a drug (or drugs) at a time other than promptly after administration. In embodiments, the conglomerate of medicinal particles are covered with a coating which delays release of the drug.

Delayed release dosage forms are known to those skilled in the art. For example, coated delayed release beads or granules in which, e.g., ketamine, norketamine, and/or other derivatives of ketamine, or a pharmaceutically acceptable salt of any of the foregoing, is applied to beads or granules, e.g., confectioners nonpareil beads, and then coated with conventional release delaying materials such as waxes, enteric coatings and the like. In embodiments, particles can be formed in which ketamine, norketamine, and/or other derivatives of ketamine, or a pharmaceutically acceptable salt of any of the foregoing, is mixed with a material to provide a mass from which the drug leaches out. In embodiments, the particles may be engineered to provide different rates of release by varying characteristics of the coating or mass, e.g., thickness, porosity, using different materials, etc. In embodiments, enteric coated granules of ketamine, norketamine, and/or other derivatives of ketamine, or a pharmaceutically acceptable salt of any of the foregoing, can be contained in an enterically coated capsule or tablet which releases the granules in the small intestine. In embodiments, the granules have a coating which remains intact until the coated granules reach at least the ileum and thereafter provide a delayed release of the drug in the colon. Suitable enteric coating materials are well known in the art, e.g., Eudragit® coatings such methacrylic acid and methyl methacrylate polymers and others. The granules can be contained in capsules or compressed into tablets.

In embodiments, ketamine, norketamine, and/or other derivatives of ketamine, or a pharmaceutically acceptable salt of any of the foregoing, is incorporated into porous inert carriers that provide delayed release profiles. In embodiments, the porous inert carriers incorporate channels or passages from which the drug diffuses into surrounding fluids. In embodiments, ketamine, norketamine, and/or other derivatives of ketamine, or a pharmaceutically acceptable salt of any of the foregoing, is incorporated into an ion-exchange resin to provide a delayed release profile. Delayed action may result from a predetermined rate of release of the drug from the resin when the drug-resin complex contacts gastrointestinal fluids and the ionic constituents dissolved therein. In embodiments, membranes are utilized to control rate of release from drug containing reservoirs. In embodiments, liquid preparations may also be utilized to provide a delayed release profile. For example, a liquid preparation consisting of solid particles dispersed throughout a liquid phase in which the particles are not soluble. The suspension is formulated to allow at least a reduction in dosing frequency as compared to that drug presented as a conventional dosage form (e.g., as a solution or a prompt drug-releasing, conventional solid dosage form). For example, a suspension of ion-exchange resin constituents or microbeads.

In embodiments, the compound is administered in combination with conventional therapy for the encephalopathies disclosed herein. For example, treatments such as low carbohydrate diet (e.g., ketogenic diets, such as classical diet, medium chain triglyceride (MCT) diet, modified Atkins diet (MAD), and low glycemic index treatment (LGIT)), intravenous immunoglobulin, steroids, elimination diet, valgus nerve stimulation, corticectomy, and multiple subpial transections.

Effective treatment of a developmental encephalopathy (e.g., Dravet syndrome) herein may be established by showing reduction in the frequency of symptoms (e.g., more than 50%) after a period of time compared with baseline. For example, after a baseline period of 1 month, the patients may be randomly allocated ketamine, norketamine, and/or other derivatives of ketamine, or a pharmaceutically acceptable salt of any of the foregoing, or placebo as add-on therapy to standard therapies, during a double-blind period of 2 months. Primary outcome measurements may include the percentage of responders on ketamine, norketamine, and/or other derivatives of ketamine, or a pharmaceutically acceptable salt of any of the foregoing, and on placebo, defined as having experienced at least a 50% reduction of symptom frequency during the second month of the double-blind period compared with baseline.

The effectiveness of ketamine, norketamine, and/or other derivatives of ketamine, or a pharmaceutically acceptable salt of any of the foregoing, for the treatment of a disclosed developmental encephalopathy, e.g., associated with Dravet syndrome or Lennox-Gastaut syndrome, may be established in other controlled studies. For example, a randomized, double-blind, placebo-controlled study consisting of a 4-week baseline period followed by a 3-week titration period and 12-week maintenance period may be used in patients age 2-54 years with a current or prior diagnosis of DS or LGS. Multiple target maintenance doses of ketamine, norketamine, and/or other derivatives of ketamine, or a pharmaceutically acceptable salt of any of the foregoing, may be tested according to patient body weight and specific dosing regime. A primary efficacy measure may include the percent reduction in the weekly frequency of symptoms, from the 4-week baseline period to 12-week maintenance period.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "treating" or "treatment" refers to alleviating, attenuating or delaying the appearance of clinical symptoms of a disease or condition in a subject that may be afflicted with or predisposed to the disease or condition, but does not yet experience or display clinical or subclinical symptoms of the disease or condition. In embodiments, treating" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating" or "treatment" may also refer to inhibiting the disease or condition, e.g., arresting or reducing its development or at least one clinical or subclinical symptom thereof. "Treating" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic treatment are two separate embodiments of the disclosure herein.

"Effective amount" or "therapeutically effective amount" means a dosage sufficient to alleviate one or more symptom of a disorder, disease, or condition being treated, or to otherwise provide a desired pharmacological and/or physiologic effect.

"Pharmaceutically acceptable" refers to molecular entities and compositions that are "generally regarded as safe"—e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s)

and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

As used herein, the term "prevention" or "preventing" means to administer a composition to a subject or a system at risk for or having a predisposition for one or more symptoms caused by a disease or disorder to facilitate cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

"PK" refers to the pharmacokinetic profile. $C_{max}$ is defined as the highest plasma drug concentration estimated during an experiment (ng/ml). $T_{max}$ is defined as the time when $C_{max}$ is estimated (min). $AUC_{0-\infty}$ is the total area under the plasma drug concentration-time curve, from drug administration until the drug is eliminated (ng·hr/ml or µg·hr/ml). The area under the curve is governed by clearance. Clearance is defined as the volume of blood or plasma that is totally cleared of its content of drug per unit time (ml/min). $F_{abs}$ refers to the absolute bioavailability. Absolute bioavailability compares the bioavailability of the active drug in systemic circulation following non-intravenous administration (e.g., after oral administration), with the bioavailability of the same drug following intravenous administration. It is the fraction of the drug absorbed through non-intravenous administration compared with the corresponding intravenous administration of the same drug. The absolute bioavailability is the dose-corrected area under curve (AUC) non-intravenous (oral) divided by AUC intravenous. For example, the formula for calculating $F_{abs}$ for a drug administered by the oral route is $$F_{abs}=AUC_{oral}/AUC_{iv} \times dose_{iv}/dose_{oral}.$$

"Prodrug", as used herein, refers to a pharmacological substance (drug) that is administered to a subject in an inactive (or significantly less active) form. Once administered, the prodrug is metabolized in the body (in vivo) into a compound having the desired pharmacological activity.

"Analog" and "Derivative" are used herein interchangeably and can refer to a compound that possesses the same core as the parent compound, but may differ from the parent compound in bond order, the absence or presence of one or more atoms and/or groups of atoms, and combinations thereof. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

"Stereoisomer", as used herein, refers to isomeric molecules that have the same molecular formula and sequence of bonded atoms (constitution), but which differ in the three dimensional orientations of their atoms in space. Examples of stereoisomers include enantiomers and diastereomers. As used herein, an enantiomer refers to one of the two mirror-image forms of an optically active or chiral molecule. Diastereomers (or diastereoisomers) are stereoisomers that are not enantiomers (non-superimposable mirror images of each other). Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Enantiomers and/or diasteromers can be resolved or separated using techniques known in the art. "Chirality" also includes axial and planar chirality.

The term "pharmaceutically acceptable salt", as used herein, applies to the compounds defined herein, wherein the parent compound is modified by making acid or base salts thereof as discussed above. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts. The pharmaceutically acceptable salts of the compounds can be synthesized from the parent compound, which contains a basic or acidic moiety, by conventional chemical methods.

EXAMPLES

The examples provided herein are included solely for augmenting the disclosure herein and should not be considered to be limiting in any respect.

Example I

Prospective Evaluation of Ketamine in Dravet Models

Mice with heterozygous mutations encompassing the Scn1a gene have been used to model Dravet syndrome. Scn1a$^{+/-}$ mice recapitulate many of the features of Dravet syndrome, including seizures provoked by elevated body temperature and cognitive deficits. The protocol outlined below will evaluate the ability of ketamine to protect against hyperthermia-induced seizures and characterize the impact of treatment on cognition in Scn1a$^{+/-}$ mice and control littermates.

Seizure Threshold.

To test the hypothesis that ketamine is protective in a Dravet Syndrome model, the effect of drug on temperature at which treated Scn1a$^{+/-}$ mice and control littermates treated animals undergo a generalized tonic-clonic (GTC) seizure will be evaluated. This effect is well characterized in mutant offspring from crossing 129.Scn1a$^{tm1Kea}$ males and C57BL/6J females and will be the focus of these studies. Scn1a$^{+/-}$ male offspring will be randomly assigned to treatment groups (0 mg/kg, 1 mg/kg, 10 mg/kg, 50 mg/kg, and 100 mg/kg) and on postnatal day 19-20 administered vehicle or drug by oral gavage. One or 24 hours later, animals will be moved to an experimental chamber and affixed with a rectal probe connected to a feedback temperature controller and heat lamp, enabling continuous monitoring and control of body temperature. Following a 5-minute acclimation period during which body temperature will held at 37.5° C., temperature will be increased gradually by 0.5° C. every 2 minutes until a generalized tonic-clonic (GTC) seizure occurs. Body temperature at the time of myoclonic (MC) and GTC seizure will be recorded for each subject. Immediately following a GTC seizure, mice will be removed from the chamber and sacrificed. A total of 180 animals will be evaluated (18 per group×5 doses×2 timepoints) and the percentage of GTC-free and MC-free subjects compared between groups using the Cox proportional hazard model. Body temperature at seizure onset will also be compared between groups by ANOVA with Tukey's post-hoc tests.

Cognition.

To characterize the effect of ketamine in cognition, experimental animals will be generated by crossing B6.Scn1a$^{tm1.1DSF}$/J males (JAX #26133) and 129S1/Sv.H-prt$^{tm1(CAG-cre)Mnn}$/J females (JAX #4302)[4]. Beginning at 3 months of age, male offspring will be evaluated using the behavioral battery outlined below. One or 24 hours before each test, animals we be treated by oral gavage (0 mg/kg, 1 mg/kg, 10 mg/kg, 50 mg/kg, and 100 mg/kg). Each test will be separated by 3-4 days. A total of 200 animals will be evaluated (10 per group×5 doses×2 timepoints×2 genotypes). Significance will be evaluated by ANOVA with Tukey's post-hoc tests.

1. Activity and anxiety: Mice are placed individually into the center of a 40 cm×40 cm×40 cm arena and distance traveled (cm), vertical activity, and perimeter/center time measured.
2. Spontaneous alternation: Mice are placed in a clear Plexiglas™ y-maze facing the center of the y, and the sequence of entries into each arm are recorded. Spontaneous alternation is determined by calculation the proportion of "triads" in which three unique arms are visited.
3. Novel arm recognition: Mice are placed in a clear Plexiglas™ y-maze with a distinctive visual cue at the end of each arm; access is initially limited to two arms. Spatial memory is evaluated by time spent in the novel arm following access.
4. Holeboard learning: Individually housed, food restricted animals are placed in an open field with a floor consisting of 16 evenly spaced holes surrounded by distinct visual cues. Following habituation, memory for food location is determined through acquisition trials and a 24-hour probe trial.
5. Barnes Maze: Animals are placed in a maze consisting of a white circular platform with 12 circular holes standing 60 cm above the floor. Learning is evaluated during acquisition, reversal, and probe trials. Percent correct and distance traveled before finding the target hole is measured during the acquisition phase. Searches over the old target hold and distance travelled before finding the novel target hole are measured during the reversal phase.

Example II

Preparation of Multi-Particulate Tablets Containing 20 mg Ketamine Hydrochloride As described in US Publication No. 2017/003570, tablets are prepared as follows:

Step 1: A spraying solution is prepared from the following ingredients:

| | |
|---|---|
| Hypromellose | 3.00 kg |
| Ketamine hydrochloride | 20.00 kg |
| Sugar spheres | 8.00 kg |
| Ethanol 96% | q.s. |
| Water, purified | q.s. |

A spraying suspension is prepared by successively dissolving hypromellose and ketamine hydrochloride in a mixture of purified water and ethanol. Sugar spheres (saccharose, particle size range (90%) 200 to 400 µm) are filled into a fluid-bed processor with a bottom-spray nozzle and preheated. The spraying suspension is then sprayed onto the sugar spheres in the fluid-bed processor, thus preparing a plurality of sugar spheres having a layer of ketamine coated thereupon. The coated sugar spheres are then sieved to remove agglomerates (vibration sieve or equivalent).

Step 2: A coating suspension is prepared from the following ingredients:

| | |
|---|---|
| Ethylcellulose | 14.54 kg |
| Hydroxypropyl cellulose | 4.00 kg |
| Triethyl citrate | 3.27 kg |
| Talc | 1.45 kg |
| Ethanol 96% | q.s |
| Water, purified | q.s |

Hydroxypropyl cellulose is dissolved in water. Ethylcellulose and ethanol are then added to the solution. Finally, triethyl citrate and talc are added and the solution is continuously stirred. The coated sugar spheres from Step 1 are filled into a fluid-bed processor and preheated. The coated solution prepared as indicated above is sprayed onto the coated sugar spheres. The pellets obtained thereby as then sieved to remove the agglomerates.

Step 3: The following ingredients are dry mixed to a blend:

| | |
|---|---|
| Pellets from Step 2 | 54.26 kg |
| Carmellose sodium | 46.00 kg |
| Microcrystalline cellulose | 55.49 kg |
| Colloidal anhydrous silica | 1.50 kg |
| Magnesium stearate | 0.75 kg |

The resulting dry blend is then compressed to tablets.
Step 4 (Optional): A tablet coating suspension is made from the following ingredients:

| | |
|---|---|
| Opadry ® II White | 1.20 kg |
| Water, purified | q.s |

31.6 kg tablets are film coated with the tablet coating suspension.

Example III

In Vivo Pharmacokinetics

A comparative bioavailability study of ketamine and norketamine after single dose administration of ketamine (in form of ketamine hydrochloride) 10, 20, 40 and 80 mg modified release tablets in fasting state and 5 mg ketamine (in form of ketamine hydrochloride) solution for infusion is described in US Publication No. 2017/003570 as follows. In the study, the $C_{max}$, $F_{abs}$, $AUC_{0-\infty}$, and $T_{max}$ are determined in vivo in healthy subjects. The modified release tablets were produced in analogy to Example 2.

Objectives

Single dose, open label, five-treatment, five-period, consecutive study with at least 7 days wash-out between the study periods. In the first treatment all subjects received a single dose of 5 mg (±)-ketamine solution for infusion within 30 min intravenously in fasting state. The orally administered single doses of (±)-ketamine modified release tablets were given in consecutively increasing doses of 10, 20, 40 and 80 mg with 240 ml of table water in fasting state. (±)-Ketamine and (±)-norketamine were measured in serum, urine and feces.

Number of Subjects, Main Criteria for Inclusion 15 analyzed, age: 18-45 years sex: male and female, ethnic origin: Caucasian, body mass index: ≥18.5 kg/m$^2$ and ≤30 kg/m$^2$, good health as evidenced by the results of the clinical examination, ECG, and the laboratory check-up, which were judged by the clinical investigator not to differ in a clinical relevant way from the normal state, heart frequency between 50 and 90 bpm, blood pressure between 140 and 100 systolic and 90 and 60 diastolic, written informed consent.

Sampling

Blood: blank, 0.167, 0.333, 0.5, 0.667, 0.833, 1, 1.5, 2, 3, 4, 6, 8, 12, 24 h after intravenous administration and blank, 0, 0.5, 1, 1.5, 2, 2.5, 3, 3.5, 4, 4.5, 5, 6, 7, 8, 12, 16, 24, 36, 48, 60 h after oral administration. Urine: 0-24 h, 24-48 h and 48-72 h. Feces: 0-120 h.

Drug Assay

Validated achiral LC-MS/MS method for (±)-ketamine and (±)-norketamine, performed in a laboratory certified according to GLP (Good Laboratory Practice).

Pharmacokinetic Results

The results are summarized in the following tables, wherein $AUC_{0-\infty}$ stands for the area under the curve from zero extrapolated to infinity, $C_{max}$ stands for the maximum plasma concentration, $T_{max}$ stands for the time to $C_{max}$, $F_{abs}$ stands for absolute bioavailability, $T_{1/2}$ stands for the apparent terminal half-life.

TABLE 1

Pharmacokinetic characteristics of (±)-ketamine after intravenous infusion (30 min) of 5 mg (±)-ketamine and oral administration of 10, 20, 40 and 80 mg ketamine PR tablets

| | | 5 mg i.v. | 10 mg | 20 mg | 40 mg | 80 mg |
|---|---|---|---|---|---|---|
| $AUC_{0-\infty}$ | ng × h/ml | 59.9 ± 13.2 | 13.5 ± 9.73 | 27.1 ± 21.9 | 75.6 ± 48.3 | 178 ± 145 |
| $C_{max}$ | ng/ml | 33.7 ± 9.74 | 1.48 ± 0.901 | 3.25 ± 2.29 | 7.64 ± 4.69 | 16.7 ± 13.4 |
| $T_{max}$ | h | — | 4.87 ± 1.22 | 5.87 ± 0.64* | 6.00 ± 0.76* | 6.07 ± 0.26* |
| $F_{abs}$ | % | — | 11.5 ± 8.09 | 11.0 ± 8.57 | 15.9 ± 9.53*† | 17.9 ± 12.3*† |
| $T_{1/2}$ | h | 6.99 ± 5.22 | 7.39 ± 4.86 | 6.09 ± 4.98 | 8.44 ± 1.54#† | 8.89 ± 1.42#† | vs. 5 mg i.v.,
*vs. 10 mg,
†vs 20 mg

TABLE 2

Pharmacokinetics of (±)-norketamine after intravenous infusion (30 min) of 5 mg (±)-ketamine and oral administration of 10, 20, 40 and 80 mg ketamine PR tablets

| | | 5 mg | 10 mg | 20 mg | 40 mg | 80 mg |
|---|---|---|---|---|---|---|
| $AUC_{0-\infty}$ | ng × h/ml | 87.7 ± 24.1 | 162 ± 39.7 | 339 ± 100 | 653 ± 164 | 1620 ± 731 |
| $C_{max}$ | ng/ml | 11.4 ± 2.85 | 13.4 ± 2.92 | 27.6 ± 6.62 | 48.7 ± 10.4 | 113 ± 53.0 |
| $T_{max}$ | h | 0.93 ± 0.32 | 4.72 ± 1.02 | 5.33 ± 0.77* | 5.67 ± 0.52* | 6.10 ± 0.60*†‡ |
| $T_{1/2}$ | h | 8.01 ± 2.35 | 7.38 ± 1.63 | 7.74 ± 3.09 | 8.25 ± 2.70† | 8.48 ± 1.56* |

*vs. 10 mg,
†vs 20 mg,
‡vs. 40 mg,
p < 0.05 (Wilcoxon test)

The maximum concentration ($C_{max}$) and the time of maximum concentration ($T_{max}$) were obtained directly from the measured concentration-time curves. The area under the concentrations-time curve ($AUC_{0-t}$) was calculated with the measured data points from the time of administration until the last quantifiable concentration by the trapezoidal formula. The AUC was assessed up to the last sampling time above the limit of quantification and is extrapolated to infinity to obtain the $AUC_{0-\infty}$ values. Apparent Terminal half-life ($T_{1/2}$) was calculated by the following equation $T_{1/2} = \ln 2/\lambda_z$. The terminal elimination rate constant ($\lambda_z$) was evaluated from the terminal slope by log-linear regression analysis. The absolute bioavailability ($F_{abs}$) was calculated by the following equation: $F_{abs} = AUC_{oral}/AUC_{iv} \times dose_{iv}/dose_{oral}$.

Those skilled in the art will recognize, or be able to ascertain using no more than routine experimentation, many equivalents to the embodiments described herein. Such equivalents are intended to be encompassed by the following claims.

What is claimed is:

1. A method of treating Lennox-Gastaut syndrome (LGS) comprising intranasally administering to a patient in need thereof a pharmaceutical composition comprising S-ketamine or a pharmaceutically acceptable salt thereof in an amount ranging from about 1 mg to about 100 mg.

2. The method of claim 1 wherein the S-ketamine or the pharmaceutically acceptable salt thereof is administered at a dosage selected from the group consisting of about 10 mg, 20 mg, 28 mg, 40 mg, 56 mg, 80 mg and 84 mg.

3. The method of claim 2 wherein the S-ketamine or the pharmaceutically acceptable salt thereof is administered at a dosage of about 28 mg.

4. The method of claim 1 wherein the pharmaceutically acceptable salt thereof is an acid addition salt.

5. The method of claim 4 wherein the acid addition salt is S-ketamine hydrochloride.

6. The method of claim 5 wherein the S-ketamine hydrochloride is administered at a dosage of about 32.3 mg.

7. The method of claim 1, wherein administration of the composition comprising S-ketamine or the pharmaceutically acceptable salt thereof provides an in vivo plasma profile comprising a $C_{max}$ less than about 38 ng/ml.

8. The method of claim 1 wherein the S-ketamine or the pharmaceutically acceptable salt thereof is administered once daily.

9. The method of claim 1 wherein the S-ketamine or the pharmaceutically acceptable salt thereof is administered once weekly.

10. The method of claim 1 wherein the S-ketamine or the pharmaceutically acceptable salt thereof is administered twice weekly.

11. The method of claim 1 wherein the amount of the S-ketamine or the pharmaceutically acceptable salt thereof is administered in an amount ranging from about 0.1 mg/kg and about 10 mg/kg of body weight of the patient.

12. The method of claim 1, wherein administration of the composition comprising S-ketamine or the pharmaceutically acceptable salt thereof provides an in vivo plasma profile comprising an $AUC_{0-\infty}$ less than about 200 ng·hr/ml.

* * * * *